United States Patent [19]

Tsuchiya et al.

[11] Patent Number: 5,397,504
[45] Date of Patent: Mar. 14, 1995

[54] BIPHENYL COMPOUND

[75] Inventors: Kazuhiko Tsuchiya; Kenji Suzuki; Atsushi Sugiura; Tsunenori Fujii, all of Soka, Japan

[73] Assignee: Kanto Kagaku Kabushiki Kaisha, Tokyo, Japan

[21] Appl. No.: 180,772

[22] Filed: Jan. 10, 1994

Related U.S. Application Data

[63] Continuation of Ser. No. 830,521, Feb. 3, 1992, abandoned, which is a continuation of Ser. No. 306,452, Jan. 27, 1989, abandoned.

[30] Foreign Application Priority Data

May 29, 1987 [JP] Japan ................................ 62-131545
Dec. 11, 1987 [JP] Japan ................................ 62-312309

[51] Int. Cl.6 ...................... C07C 69/00; C07C 41/00; C09K 19/12
[52] U.S. Cl. ............................... 252/299.66; 560/141; 568/642
[58] Field of Search ...................... 252/299.01, 299.66; 359/104; 560/141; 568/642, 647

[56] References Cited

U.S. PATENT DOCUMENTS

| | | | |
|---|---|---|---|
| 4,490,305 | 12/1984 | Eidenschink et al. | 252/299.66 |
| 4,544,771 | 10/1987 | Romer et al. | 252/299.66 |
| 4,576,732 | 3/1986 | Isogai et al. | 252/299.65 |
| 4,592,858 | 6/1986 | Higuchi et al. | 252/299.66 |
| 4,596,667 | 6/1986 | Inukai et al. | 252/299.65 |
| 4,614,609 | 9/1986 | Inoue et al. | 252/299.65 |
| 4,650,600 | 3/1987 | Heppke et al. | 252/299.66 |
| 4,676,925 | 6/1987 | Inoue et al. | 252/299.65 |
| 4,753,752 | 6/1988 | Raynes et al. | 252/299.66 |
| 4,795,579 | 1/1989 | Vauchier | 252/299.66 |
| 4,808,333 | 2/1989 | Huynh-Ba et al. | 252/299.66 |
| 4,818,432 | 4/1989 | Miyazawa et al. | 252/299.66 |

FOREIGN PATENT DOCUMENTS

| | | |
|---|---|---|
| 0074608 | 9/1982 | European Pat. Off. . |
| 0084194 | 7/1983 | European Pat. Off. . |
| 0188222 | 7/1986 | European Pat. Off. . |
| 0243209 | 10/1987 | European Pat. Off. . |
| 0256307 | 2/1988 | European Pat. Off. . |
| 0269062 | 6/1988 | European Pat. Off. . |
| 0272115 | 6/1988 | European Pat. Off. . |
| 58-121225 | 7/1983 | Japan . |
| 58-126823 | 7/1983 | Japan . |
| 58-162549 | 9/1983 | Japan . |
| 59-76029 | 4/1984 | Japan . |
| 59-118744 | 7/1984 | Japan . |
| 59-219251 | 12/1984 | Japan . |
| 60-13729 | 1/1985 | Japan . |
| 60-51147 | 3/1985 | Japan . |
| 60-218358 | 11/1985 | Japan . |
| 61-249953 | 11/1986 | Japan . |
| 62-56455 | 3/1987 | Japan . |
| 62-187421 | 8/1987 | Japan . |
| 62-255446 | 11/1987 | Japan . |
| 63-22533 | 1/1988 | Japan . |

OTHER PUBLICATIONS

Meyer et al., J. Physique, 36, L–69 (1975).
Clark et al., Appl. Phys. Lett. 36, 899 (1980).

*Primary Examiner*—Philip Tucker
*Attorney, Agent, or Firm*—Birch, Stewart, Kolasch & Birch

[57] ABSTRACT

A new biphenyl compound which is chemically stable and possesses practically excellent properties as a component for preparing ferroelectric smetic liquid crystalline compositions as well as a new liquid crystalline composition containing this compound.

8 Claims, No Drawings

BIPHENYL COMPOUND

This application is a continuation of application Ser. No. 07/830,521, filed on Feb. 3, 1992, now abandoned, which is a continuation of application Ser. No. 07/306,452, filed on Jan. 27, 1989, now abandoned.

BRIEF DESCRIPTION OF THE INVENTION

The present invention relates to new liquid crystalline compounds as well as liquid crystalline compositions containing at least one of the liquid crystalline compounds. More particularly, the present invention relates to ferroelectric smectic liquid crystals and to new biphenyl compounds which are useful as components for preparing practical ferroelectric smectic liquid crystalline compositions and excellent in chemical stability as well as liquid crystalline compositions containing at least one of the biphenyl compounds.

TECHNICAL BACKGROUND

At present, various kinds of display elements are used in practice among which liquid crystalline display elements have such beneficial characteristics as no eyestrain because of their light-receiving property, extremely low consumption of electric power, a thin structure, etc. and are widely utilized for watches, electronic desk computers, personal word processors, etc. However, these display elements utilize nematic liquid crystals and so have a shortcoming that they are slow in response speed. Although various studies have been made to overcome this shortcoming, a satisfactory improvement has not yet been made to overcome this shortcoming.

For the above reasons, studies different from those using nematic liquid crystals are also actively made, one of which uses strongly dielectric liquid crystals.

The ferroelectric smectic liquid crystals were found by R. B. Meyer et al. [J. Physique, 36, L-69(1975)]. As the ferroelectric smectic liquid crystals enable high speed response as compared to the nematic liquid crystals, studies for display elements using the strongly dielectric liquid crystals have now been actively made [N. A. Clark, S. T. Lagerwall Appl. Phys. Lett. 36, 899(1980)].

As the display of this type utilizes ferroelectric smectic liquid crystals, i.e. chiral smectic C phase (referred to hereinafter briefly as SmC* phase) and chiral smectic H phase (referred to hereinafter briefly as SmH* phase), liquid crystalline substances in which these phases exist at around room temperature are desired.

As in the case of nematic liquid crystals, the ferroelectric smectic liquid crystals for display elements are not used singly but are used as a composition comprising plural kinds of ferroelectric smectic liquid crystals.

Generally, suitably selected single compounds are mixed to prepare a composition having the required properties. Among known compounds, however, the number of ferroelectric smectic liquid crystalline compounds utilizable as ingredients for such composition is extremely small. Accordingly, development of new compounds, especially substances having a ferroelectric smectic liquid crystalline phase at about room temperature is desired and strongly demanded. It is an object of the present invention to provide new substances satisfy such demand.

Among the known biphenyl compounds having a similar structure, those having no substituent on their benzene rings are disclosed, for example, in Japanese Laid-open Patent Appln. Nos. Sho. 59-118744, 62-56455, 60-218358, 60-13729, 62-187421, 63-22533, 59-219251 and 60-51147, and those having a halogen atom or atoms on their benzene rings are disclosed, for example, in Japanese Laid-open Patent Appln. Nos. Sho. 61-249953 and 62-255446.

The present invention provides substances having a ferroelectric smectic liquid crystalline phase at about room temperature and being excellent in practical value as compared with these compounds.

DETAILED DESCRIPTION OF THE INVENTION

The present invention provides an optically active biphenyl compound of the formula:

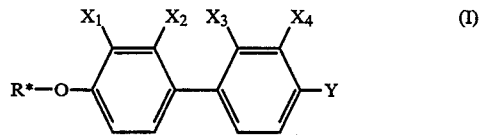

wherein R* is an alkyl group having an asymmetric carbon atom and 4–14 carbon atoms, any one or two of $X_1$, $X_2$, $X_3$ and $X_4$ is/are a fluorine or chlorine atom/atoms and the others hydrogen atoms, and Y is R, OR, COOR or OCOR where R is an alkyl group with 3–14 carbon atoms, with the proviso that when $X_1$ is a halogen atom, Y should not be R, and a liquid crystalline composition characterized by containing at least one of these compounds. The new ferroelectric smectic liquid crystalline compounds themselves of the present invention possess a broad SmC* phase at room temperature range, but the temperature range of the SmC* phase can further be broadened by making a mixture of the compounds of the above formula (I) or adding the compounds to other compositions. The new biphenyl derivatives of the present invention are substances effectively utilizable for broadening the working temperature range of display elements.

The compounds of the present invention can be synthesized through a synthesis route as will be shown hereinafter according to chemical synthetic reactions and synthetic methods known per se.

The chemical synthetic reactions and synthetic methods known from the past are, for example, reactions and methods disclosed in Houben-Weyl, Methoden der Organischen Chemie, etc. which are widely known in this art.

The present invention will now be explained in more detail, showing the synthetic route and examples for the preparation of the new compounds concerned with the present invention.

The new biphenyl compounds of the present invention can be synthesized through a plurality of routes, for example, according to the routes shown below.

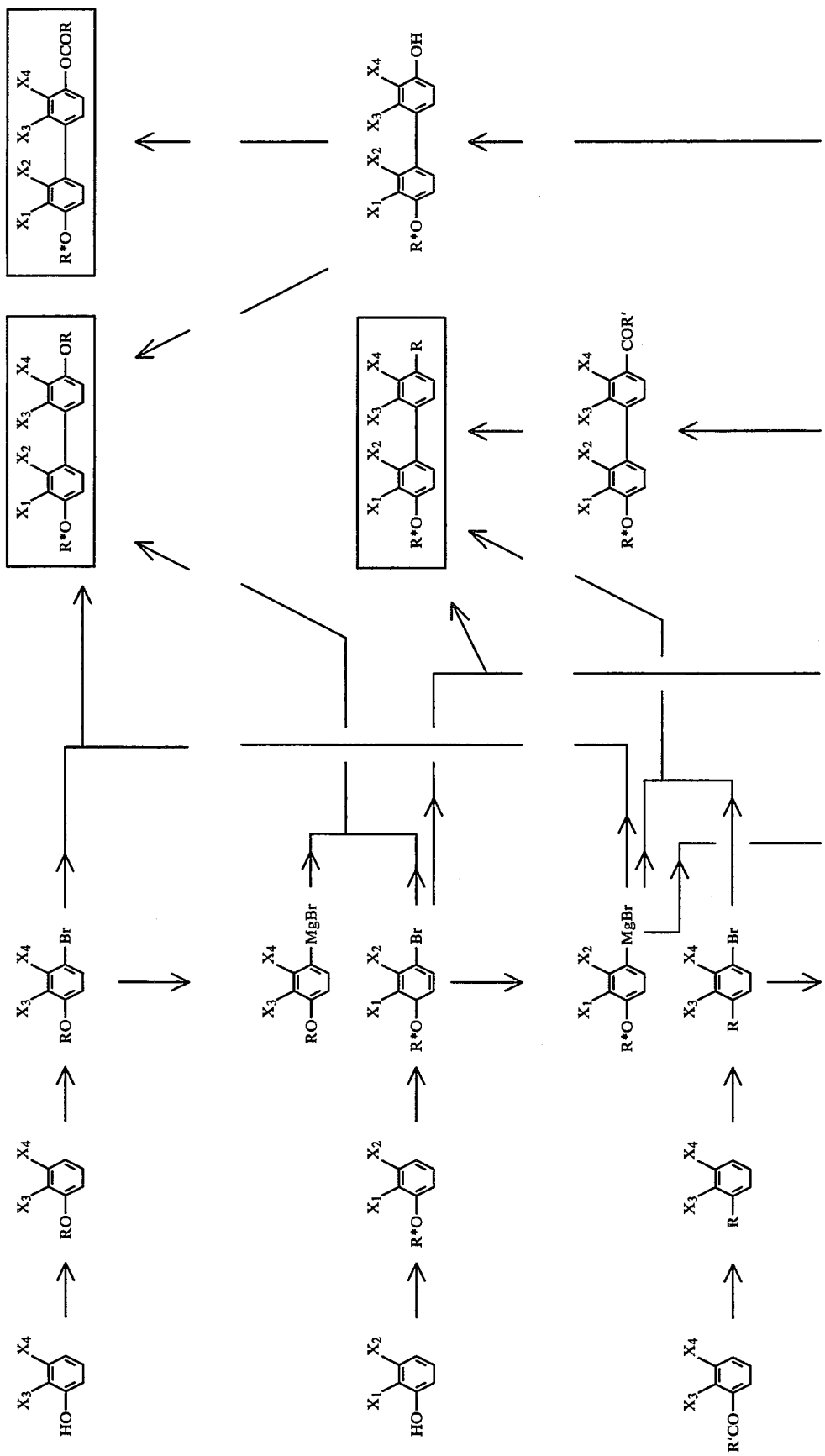
Diagram of Synthesis route 1

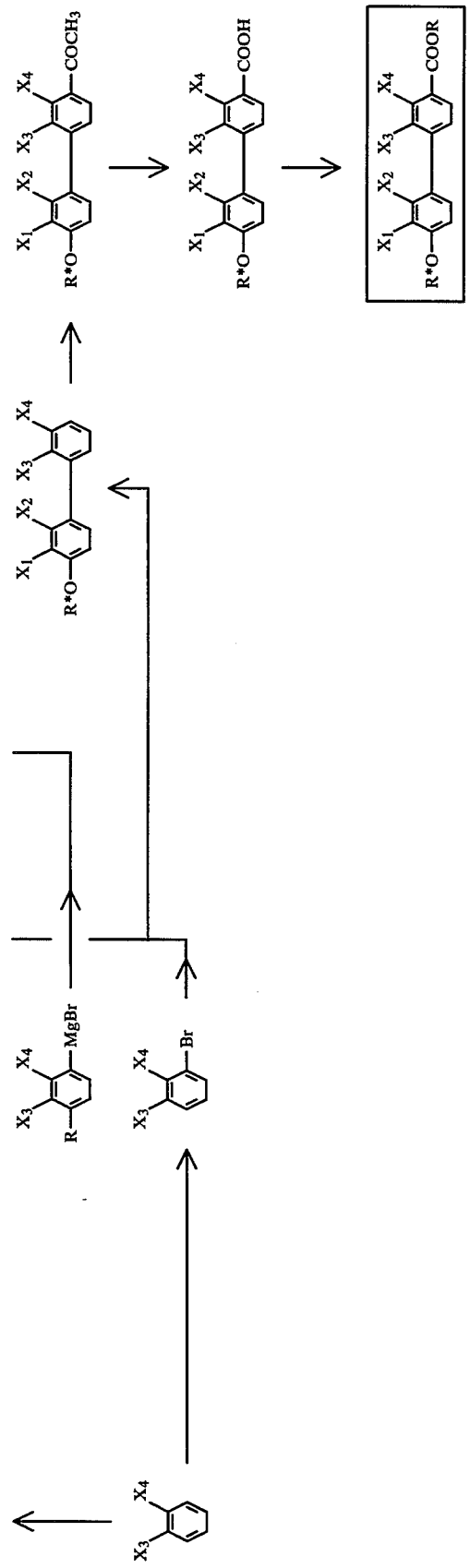

Diagram of Synthesis route 2
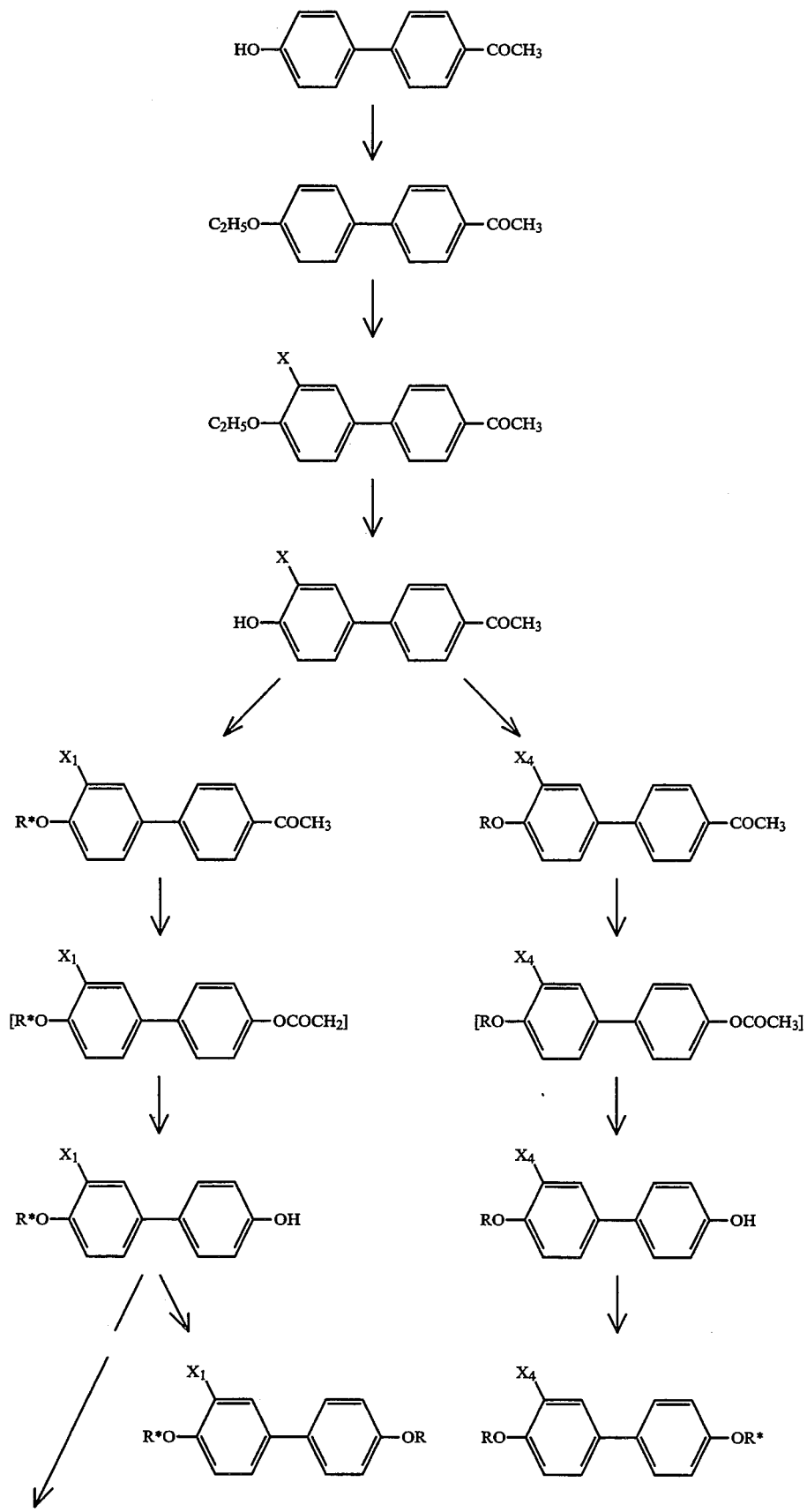

-continued
Diagram of Synthesis route 2

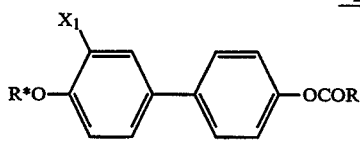

(X = X₁ = X₄ = chlorine atom)

The following examples illustrate the compounds of this invention and the preparation thereof, wherein the notations and abbreviations used are as follows:
TLC: thin layer chromatography
HPLC: high speed liquid chromatography
GLC: gas chromatography
I.R.: infra-red rays absorption spectra
Mass: Mass spectra
b.p.: boiling point
m.p.: melting point
C: crystals
$S_X$, SmX: unidentified smectic phase
$S_C^*$, SmC*: chiral smectic phase
$S_A$, SmA: smectic A phase
Cho: choresteric phase
I: isotropic liquid
?: temperature being indefinite It is ordinary that the phase transition temperature more or less varies in its value according to the measuring method and purity of the substance to be measured. The values given in the examples are shown as an average value of the values obtained in experiments.

EXAMPLE 1

(a) Synthesis of

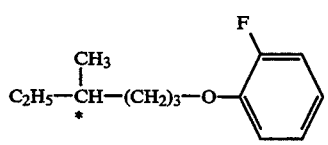

A reaction vessel was charged with 19 g of decyl bromide, 15 g of 4-bromophenol, 24 g of $K_2CO_3$ and 150 ml of cyclohexanone, and the mixture was heated with stirring for 9 hours at 120°–130° C.

After completion of the reaction, a solid matter was filtered off by suction and the filtrate was washed with water and dried over Glauber's salt. The cyclohexanone was distilled off and the residue was distilled under reduced pressure whereby 24 g of 4-bromodecyloxybenzene was obtained.
b.p. 152°–163° C./1 mmHg
GLC at least 92%

(b) Synthesis of

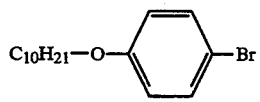

A reaction vessel was charged with 20 g of (s)-4-methylhexyl bromide, 12 g of 2-fluorophenol, 24 g of $K_2CO_3$ and 150 ml of cyclohexanone, and the mixture was heated with stirring for 11 hours at 120°–130° C.

After completion of the reaction, a solid matter was filtered off by suction and the filtrate was washed with water and dried over Glauber's salt. The solvent was distilled off and the residue was distilled under reduced pressure whereby 22 g of of (s)-2-fluoro-(4'-methylhexyl)-oxybenzene was obtained.
b.p. 81°–90° C./0.6 mmHg
GLC at least 98%

(c) Synthesis of

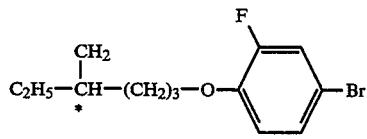

A reaction vessel was charged with 20 g of the (s)-2-fluoro-(4'-methylhexyl)oxybenzene obtained in the above (b) and 50 ml of chloroform. To this mixture was added with stirring 16 g of $Br_2$ at room temperature. The stirring was continued for 4 hours, and the reaction mixture was poured into an aqueous solution of NaOH. The organic layer separated was washed with water and dried over Glauber's salt.

The solvent was distilled off and the residue was distilled under reduced pressure whereby 20 g of (a)-2-fluoro-4-bromo-(4'-methylhexyl)oxybenzene was obtained.
b.p. 88°–94° C./0.15 mmHg
GLC at least 97%

(d) Synthesis of

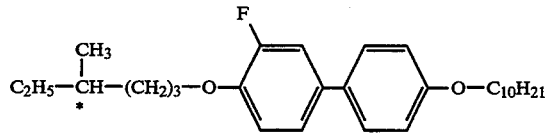

A reaction vessel was charged with 0.84 g of Mg, and a proper amount of a solution of 11 g of 4-bromodecyl-oxybenzene obtained in the above (a) in 20 ml of THF was poured thereinto. A small piece of $I_2$ was then added and the mixture was warmed to initiate reaction. The remaining THF solution was slowly added dropwise to the mixture under reflux and agitation. After the addition, the mixture was refluxed for 2 hours to prepare a Grignard reagent.

A separate vessel was charged with 0.2 g of $Cl_2Pd(PPh_3)_2$ and 50 ml of THF, and 2 of a 1M solution of (iso-$C_4H_9)_2$AlH/hexane was added thereto in a stream of $N_2$. To this mixture was added a solution of 10 g of (s)-2-fluoro-4-bromo-(4'-methylhexyl)oxybenzene obtained in the above (c) in 30 ml of THF. This mixture was warmed, and the Grignard reagent previously prepared was added dropwise thereto at 50°–55° C. The reaction liquid was aged for 2 hours at the same temperature, poured into diluted hydrochloric acid and extracted with benzene. The extract was washed with water and dried over Glauber's salt. The benzene was distilled off and the residue was purified by way of column chromatography on silica gel using hexanebenzene (10:1) as eluent. The resultant crystals were recrystallized from acetone to give 1.7 g of (s)-4-decyloxy-3'-fluoro-4'-(4''-methylhexyl)oxybiphenyl.

The purity of this compound was confirmed to be at least 99% by liquid chromatography. This compound was confirmed to be the end product in view of its measurement by infra-red absorption spectrometry and its molecular ion peak found at 442 by mass spectrometry and in view of the relation to the starting materials used.

This compound was inserted into a Mettler hot stage FP-82 and its phase transition was observed under a polarization microscope. A result of the observation is shown in Table 1.

EXAMPLE 2

(a) Synthesis of

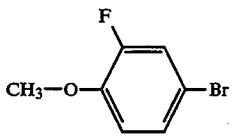

A reaction vessel was charged with 128 g (1.016 mol) of 2-fluoroanisole and 250 ml of chloroform. To this mixture was added dropwise under agitation at room temperature 177 g (1.106 mol) of bromine over the period of at least 3 hours. The reaction liquid was poured into a diluted aqueous solution of NaOH, and the chloroform layer was separated, washed with a solution of edible salt and dried over Glauber's salt. The solvent was distilled off and the residue was distilled under reduced pressure to obtain 2-fluoro-4-bromoanisole.

Yield 192 g (yield rate: 92.3% )
b.p. 107°–116° C./25–31 mmHg (b) Synthesis of

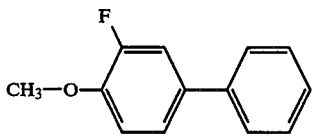

A reaction vessel was charged with 22 g (0.905 mol) of magnesium, a small amount of iodine and 50 ml of THF in a stream of nitrogen. Into this mixture was poured a proper amount of a solution of 144 g (0.917 mol ) of bromobenzene in 150 ml of THF, and the mixture was then warmed. After initiation of the reaction, the remaining THF solution was added dropwise to the mixture under reflux and agitation. After the addition, the mixture was refluxed for 2 hours to prepare a Grignard reagent.

A separate vessel was charged with 3.6 g of $Cl_2Pd(PPh_3)_2$ and 100 ml of THF. To the mixture were added in a stream of nitrogen 26 ml of a 1 mol solution of $(iso-C_4H_9)_2AlH$/hexane and then a solution of 120 g (0.585 mol) of 2-fluoro-4-bromoanisole obtained in (a) in 150 ml of THF.

The mixture was warmed and the previously prepared Grignard reagent was added dropwise thereto at 50°–60° C. The mixture was aged for 2 hours at the same temperature. After completion of the reaction, the reaction liquid was poured into diluted hydrochloric acid and extracted with benzene. The extract was washed with water and dried over Glauber's salt. The solvent was distilled off and the residue was recrystallized from a mixed solvent of chloroform-hexane and then purified by way of column chromatography on silica gel using hexane as an eluent whereby 3-fluoro-4-methoxybiphenyl was obtained.

Yield 96 g (81.3%)
GLC at least 98%

(c) Synthesis of

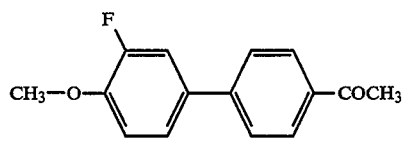

A reaction vessel was charged with 95 g (0.470 mol) of 3-fluoro-4-methoxybiphenyl obtained in (b) and 400 ml of methylene chloride. To this mixture was added under agitation below 0° C. 94 g (0.705 mol) of anhydrous aluminum chloride in small portions and was then added dropwise 56 g (0.705 mol) of acetyl chloride. After the addition, the mixture was stirred for 6 hours while elevating the temperature gradually. The reaction liquid was poured into diluted hydrochloric acid, and the organic layer was washed with water and dried over Glauber's salt. The solvent was distilled off and the residue was recrystallized from chloroform to obtain 3-fluoro-4-methoxy-4'-acetylbiphenyl.

Yield 114 g (99.3%)
GLC at least 99%

(d) Synthesis of

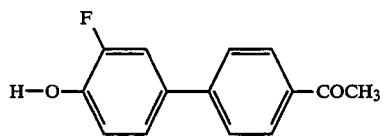

A reaction vessel was charged with 84 g (0.344 mol) of 3-fluoro-4-methoxy-4'-acetylbiphenyl obtained in (c), 700 ml of 48% hydrobromic acid and 900 ml of acetic acid, and the mixture was heated with stirring for 12 hours at 100°–110° C. The reaction liquid was poured into water and the precipitated crystals were collected by filtration, washed with water and purified by way of column chromatography on silica gel using methylene chloride as an eluent whereupon 3-fluoro-4-hydroxy-4'-acetylbiphenyl was obtained.

Yield 58 g (73.2%)
GLC at least 99%

(e) Synthesis of

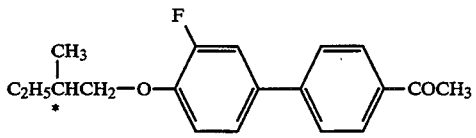

A reaction vessel was charged with 12.6 g of 3-fluoro-4-hydroxy-4'-acetylbiphenyl obtained in (d), 9.3 g of (s)-2-methylbutyl bromide, 15.1 g of potassium carbonate and 200 ml of cyclohexanone, and the mixture was heated with stirring for 20 hours at 90°-100° C. The reaction liquid was filtered and the solid matter obtained was washed with benzene. The filtrate and the washing were combined, washed with water and then dried over Glauber's salt.

The solvents were distilled off and the residue was recrystallized from acetone-methanol whereupon (s)-3-fluoro-4-(2''-methylbutyl)oxy-4'-acetylbiphenyl was obtained.

Yield 10.8 g (65.5%)
GLC at least 99%

(f) Synthesis of

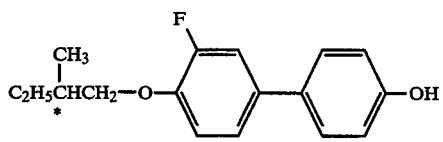

A reaction vessel was charged with 8.0 g of (s)-3-fluoro-4-(2''-methylbutyl)oxy-4'-acetylbiphenyl obtained in (e), 36 g of 88% formic acid and 90 ml of methylene chloride. To the mixture were successively added dropwise under agitation at room temperature 16 g of acetic anhydride, 1.0 ml of concentrated sulfuric acid and 30 g of 35% hydrogen peroxide. After the addition, the mixture was refluxed until the starting material disappeared in TLC (Kieselgel 60F254, developing liquid: benzene). The reaction liquid was poured into water and the mixture was stirred for 1 hour. The organic layer was washed with water until the washing liquid became neutral and then dried over Glauber's salt. The solvent was distilled off, and 70 ml of methanol and 20 ml of a 40% aqueous solution of KOH were added to the resultant residue. The mixture was reacted together for 3 hours at 70° C. under agitation. The reaction liquid was poured into water, and the mixture was made acidic with hydrochloric acid. The mixture was extracted with ether, and the extract was washed with water and dried over Glauber's salt. The solvent was distilled off and the residue was purified by way of column chromatography on silica gel whereupon (s)-3-fluoro-4-(2''-methylbutyl)-4'-hydroxybiphenyl was obtained.

Yield 5.2 g (71.2%)
GLC at least 98%

(g) Synthesis of

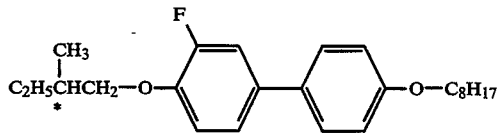

A reaction vessel was charged with 1.5 g of (s)-3-fluoro-4-(2''-methylbutyl)oxy-4'-hydroxybiphenyl obtained in (f), 2.0 g of octyl bromide, 1.35 g of potassium carbonate and 25 ml of cyclohexanone, and the mixture was reacted together for 15 hours at 90°-100° C. The reaction liquid was filtered and the resultant solid matter was washed with benzene. The filtrate and the washing liquid were combined, washed with water and dried over Glauber's salt. The solvents were distilled off and the resultant residue was recrystallized from acetone-methanol to obtain (s)-3-fluoro-4-(2''-methylbutyl)oxy-4'-octyloxybiphenyl.

Yield 0.9 g (47.6%)

The purity of this compound was at least 99% by liquid chromatography. The resultant compound was confirmed to be the end product in view of its measurement by infra-red absorption spectrometry and its molecular ion peak found at 386 by mass spectrometry and in view of the relation to the starting materials used.

This compound was inserted into a Mettler hot stage FP-82 and its phase transition was observed under a polarization microscope. A result of the observation is shown in Table 1.

EXAMPLES 3, 4 and 5

Except that 1.8 g of pentyl bromide, 2.2 g of decyl bromide or 2.4 g of dodecyl bromide was used in place of 2.0 g of octyl bromide in Example 2-(g), an operation was carried out in a similar manner whereby the corresponding compounds shown by the following formulas were obtained in a yield of 1.0 g (56.2%), 0.7 g (34.5%) or 1.5 g (70%), respectively.

The purity of these compounds were at least 99% by liquid chromatography. These compounds were confirmed to be the end products in view of measurement by infra-red absorption spectrometry and their molecular ion peaks found at 344, 414 and 442, respectively, by mass spectrometry and in view of the relation to the starting materials used.

These compounds were inserted into a Mettler hot stage FP-82 and their phase transition was observed under a polarization microscope. Results of the observation are shown in Table 1.

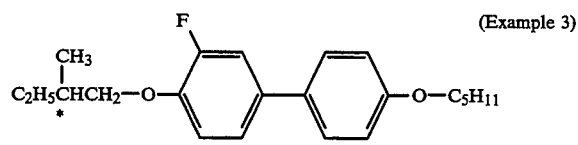
(Example 3)

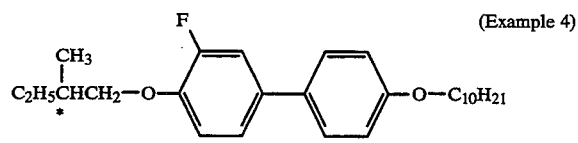
(Example 4)

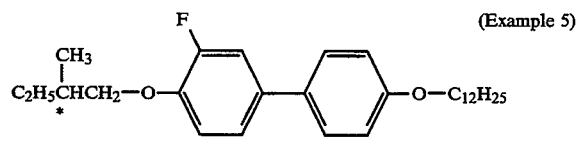
(Example 5)

EXAMPLE 6

(a) Synthesis of

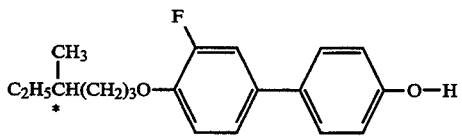

Except that 10.7 g of (s)-4-methylhexyl bromide was used in place of 9.3 g of (s)-2-methylbutyl bromide in Example 2-(e), an operation was carried out in a similar manner whereby (s)-3-fluoro-4-(4''-methylhexyl)oxy-4'-acetylbiphenyl was obtained in a yield of 15 g (70%). Except that 9.2 g of this compound was used in place of 8.0 g of (s)-3-fluoro-4-(2''-methylbutyl)oxy-4'-acetylbiphenyl in Example 2-(f), an operation was carried out in a similar manner whereby (s)-3-fluoro-4-(4''-methylhexyl)oxy-4'-hydroxybiphenyl was obtained.

Yield 5.7 g (66.8%) was obtained.
GLC at least 97%

(b) Synthesis of

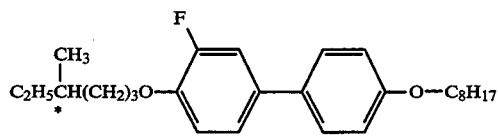

A reaction vessel was charged with 1.5 g of (s)-3-fluoro-4-(4''-methylhexyl)oxy-4'-hydroxybiphenyl obtained in the above (a), 1.1 g of octyl bromide, 1.71 g of potassium carbonate and 20 ml of cyclohexanone, and the mixture was reacted together for 15 hours at 90°-100° C. The reaction liquid was filtered and the resultant solid matter was washed with benzene. The filtrate was combined with the washing liquid, washed with water and dried over Glauber's salt. The solvents were distilled off and the resultant residue was recrystallized from acetonemethanol to obtain (s)-3-fluoro-4-(4''-methylhexyl)oxy-4'-octyloxybiphenyl.

Yield 1.0 g (48.1%)

The purity of this compound was at least 99% by liquid chromatography. This compound was confirmed to be the end product in view of its measurement by infra-red absorption spectrometry and its molecular ion peak found at 414 by mass spectrometry and in view of the relation to the starting materials used.

This compound was inserted into a Mettler hot stage FP-82 and its phase transition was observed under a polarization microscope. A result of the observation is shown in Table 1.

EXAMPLE 7

Synthesis of

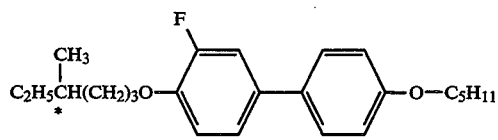

Except that 0.85 g of pentyl bromide was used in place of 1.1 g of octyl bromide in Example 6-(b), an operation was carried out in a similar manner to obtain (s)-3-fluoro-4-(4''-methylhexyl)oxy-4'-pentyloxybiphenyl.

Yield 1.4 g (76.8%)

The purity of this compound was at least 99% by liquid chromatography. This compound was confirmed to be the end product in view of its measurement by infra-red rays absorption spectrometry and its molecular ion peak found at 372 by mass spectrometry and in view of the reaction to the starting materials used.

This compound was inserted into a Mettler hot stage FP-82 and its phase transition was observed under a polarization microscope. A result of the observation is shown in Table 1.

EXAMPLE 8

(a) Synthesis of

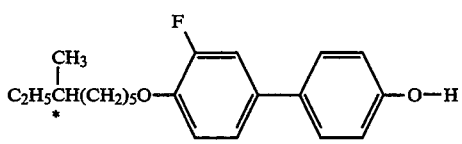

Except that 12.7 g of (s)-6-methyloctyl bromide was used in place of 9.3 g of (s)-2-methylbutyl bromide in Example 2-(e), an operation was carried out in a similar manner whereby (s)-3-fluoro-4-(6''-methyloctyl)oxy-4'-acetylbiphenyl was obtained in a yield of 13.1 g (67%). Except that 10 g of this compound was used in place of 8.0 g of (s)-3-fluoro-4-(2''-methylbutyl)oxy-4'-acetylbiphenyl in Example 2-(f), an operation was carried out in a similar manner whereby (s)-3-fluoro-4-(6''-methyloctyl)oxy-4'-hydroxybiphenyl was obtained in a yield of 2.7 g (29%).

GLC at least 99%

(b) Synthesis of

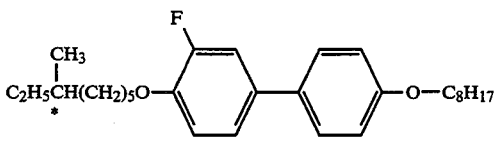

A reaction vessel was charged with 1.0 g of (s)-3-fluoro-4-(4''-methyloctyl)oxy-4'-hydroxybiphenyl obtained in the above (a), 1.2 g of octyl bromide, 1.0 g of potassium carbonate and 25 ml of cyclohexanone, and the mixture was reacted together for 15 hours at 90°-100° C. The reaction liquid was filtered and the resultant solid matter was washed with benzene. The filtrate and the washing liquid were combined, washed with water and dried over Glauber's salt. The solvents were removed by distillation and the resultant residue was recrystallized from acetone-methanol to obtain (s)-3-fluoro-4-(4'' -methyloctyl)oxy-4'-octyloxybiphenyl.

Yield 0.84 g (63.2%)

The purity of this compound was at least 99% by liquid chromatography. Further, this compound was confirmed to be the end product in view of its measurement by infra-red rays absorption spectrometry and its molecular ion peak found at 442 by mass spectrometry and in view of the relation to the starting materials used.

This compound was inserted into a Mettler hot stage FP-82 and its phase transition was observed under a polarization microscope. A result of the observation is shown in Table 1.

EXAMPLES 9 and 10

Synthesis of (Example 9)

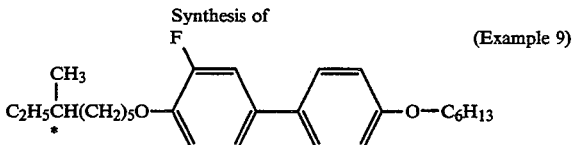

Synthesis of

-continued

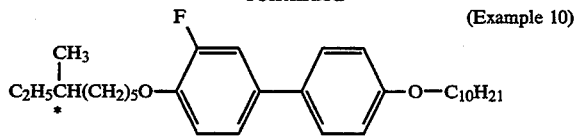
(Example 10)

Except that 1.0 g of hexyl bromide or 0.8 g of decyl bromide were used in place of 1.2 g of octyl bromide in Example 8-(b), an operation was carried out in a similar manner whereby 1.1 g (yield: 88%) or 0.65 g (yield: 93%) of the corresponding (s)-3-fluoro-4-(6''-methyloctyl)oxy-4'-hexyloxybiphenyl or (s)-3-fluoro-4-(6''-methyloctyl)oxy- 4'-decyloxybiphenyl, respectively, was obtained.

The purity of these were at least 99% by liquid chromatography. The obtained substances were confirmed to the end products in view of their measurements by infra-red rays absorption spectrometry and their molecular ion peaks found at 414 and 470 by mass spectrometry and in view of the relation to the starting materials used.

These were inserted into a Mettler hot stage FP-82 and their phase transition was observed under a polarization microscope. Result of the observation are shown in Table 1.

EXAMPLE 11

(a) Synthesis of

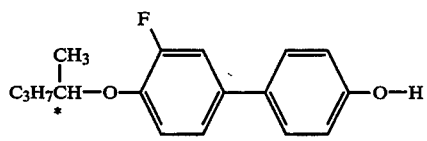

Except that 14.9 g of (s)-1-methylbutyl tosylate was used in place of 9.3 g of (s)-2-methylbutyl bromide in Example 2-(e), an operation was carried out in a similar manner whereby (s)-3-fluoro-4-(1''-methylbutyl)oxy-4'-acetylbiphenyl was obtained in a yield of 10.2 g (yield rate: 62%). Except that 8 g of this compound was used in place of 8 g of (s)-3-fluoro-4-(2''-methylbutyl)oxy-4'-acetylbiphenyl in Example 2-(f), an operation was carried out in a similar manner whereby (s)-3-fluoro-4-(1''-methylbutyl)oxy-4'-hydroxybiphenyl was obtained in a yield of 5.0 g (yield rate: 65.3%).

GLC at least 97%.

(b) Synthesis of

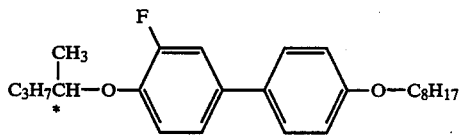

A reaction vessel was charged with 1.0 g of (s)-3-fluoro-4-(1''-methylbutyl)oxy-4'-hydroxybiphenyl, 1.4 g of octyl bromide, 1.0 g of potassium carbonate and 25 ml of cyclohexanone, and the mixture was reacted together for 15 hours at 90°–100° C. The reaction liquid was filtered and the resultant solid matter was washed with benzene. The filtrate and the washing liquid were combined, washed with water and dried over Glauber's salt. The solvents were distilled off and the residue was recrystallized from acetone-methanol to obtain (s)-3-fluoro-4-(1''-methylbutyl)oxy-4'-octyloxybiphenyl.

Yield 0.6 g (43.2%)

The purity of this compound was at least 99% by liquid chromatography. This compound was confirmed to be the end product in view of its measurement by infra-red rays absorption spectrometry and its molecular ion peak found at 386 by mass spectrometry and in view of the relation to the starting materials used.

This compound was inserted into a Mettler hot stage FP-82 and its phase transition was observed under a polarization microscope. A result of the observation is shown in Table 1.

EXAMPLES 12 and 13

Synthesis of

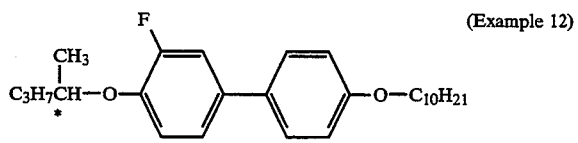
(Example 12)

Synthesis of

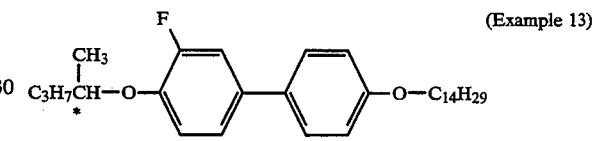
(Example 13)

Except that 1.6 g of decyl bromide or 2.0 g of tetradecyl bromide was used in place of 1.4 g of octyl bromide in Example 11-(b), an operation was carried out in a similar manner whereby 0.7 g (yield: 47%) or 0.8 g (yield: 47%) of the corresponding (s)-3-fluoro-4-(1''-methylbutyl)oxy-4'-decyloxybiphenyl or (s)-3-fluoro-4-(1''-methylbutyl)oxy-4'-tetradecyloxybiphenyl, respectively, was obtained.

The purity of these was at least 99% by liquid chromatography. These substances were confirmed to be the end products in view of their measurement by infra-red rays absorption spectrometry and their molecular ion peaks found at 414 and 470 by mass spectrometry and in view of the relation to the starting materials used.

These compounds were inserted into a Mettler hot stage FP-82 and their phase transition was observed under a polarization microscope. Result of the observations are shown in Table 1.

EXAMPLE 14

(a) Synthesis of

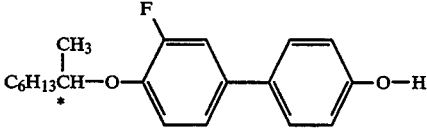

Except that 18 g of (s)-1-methylheptyl tosylate was used in place of 9.3 g of (s)-2-methylbutyl bromide in Example 2-(e), an operation was carried out in a similar manner whereby 9.1 g (yield: 46.8%) of (s)-3-fluoro-4-(1''-methylheptyl)oxy-4'-acetylbiphenyl was obtained. Except that 9.1 g of this compound was used in place of 8.0 g of (s)-3-fluoro-4-(2''-methylbutyl)oxy-4'-acetylbiphenyl in Example 2-(f), an operation was carried out in a similar manner to obtain 3.2 g (yield: 37.9%) of (s)-3-fluoro-4-(1″-methylheptyl)oxy-4′-hydroxybiphenyl.

(b) Synthesis of

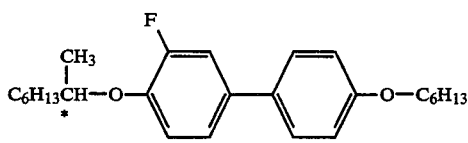

A reaction vessel was charged with 1.4 g of (s)-3-fluoro-4-(1″-methylheptyl)oxy-4′-hydroxybiphenyl obtained in the above (a), 2.0 g of hexyl bromide, 1.9 g of potassium carbonate and 25 ml of cyclohexanone, and the mixture was reacted together for 15 hours at 90°–100° C. The reaction liquid was filtered and the resultant solid matter was washed with benzene. The filtrate and the washing liquid were combined, washed with water and dried over Glauber's salt. The solvents were distilled off and the residue obtained was recrystallized from acetone-ethanol to obtain (s)-3-fluoro-4-(1″-methylheptyl)oxy-4′-hexyloxybiphenyl.

Yield 1.2 g (69%)

The purity of this compound was at least 99% by liquid chromatography. This compound was confirmed to be the end product in view of its measurement by infra-red rays absorption spectrometry and its molecular ion peak found at 400 by mass spectrometry and in view of the relation to the starting materials used.

This compound was inserted into a Mettler hot stage FP-82 and its phase transition was observed under a polarization microscope. A result of the observation is shown in Table 1.

EXAMPLE 15

Synthesis of

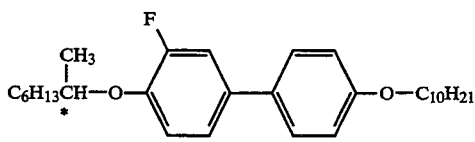

Except that 1.8 g of decyl bromide was used in place of 2.0 g of hexyl bromide in Example 14-(b), an operation was carried out in a similar manner whereby 1.2 g (yield: 60%) of (s)-3-fluoro-4-(1″-methylheptyl)oxy-4′-decyloxybiphenyl was obtained.

The purity of this compound was at least 99% by liquid chromatography. This compound was confirmed to be the end product in view of its measurement by infra-red rays absorption spectrometry and its molecular ion peak found at 456 by mass spectrometry and in view of the relation to the starting materials used.

This compound was inserted into a Mettler hot stage FP-82 and its phase transition was observed under a polarization microscope. A result of the observation is shown in Table 1.

EXAMPLE 16

(a) Synthesis of

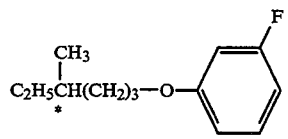

Using 3-fluorophenol similarly in place of 2-fluorophenol in Example 1-(b), 20 g of (s)-3-fluoro-(4′-methylhexyl)oxybenzene was obtained.

b.p. 109°–110° C./5 mmHg

GLC at least 99%

(b) Synthesis of

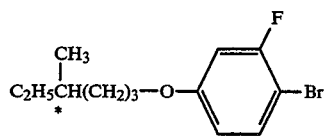

Using (s)-3-fluoro-(4′-methylhexyl)oxybenzene obtained in the above (a) similarly in place of (s)-2-fluoro-(4′-methylhexyl)oxybenzene in Example 1-(c), 21 g of (s)-3-fluoro-4-(4′-methylhexyl)oxybenzene was obtained.

b.p. 114°–121° C./ mmHg

GLC 76% (others were structurally isomeric brominated compounds)

(c) Synthesis of

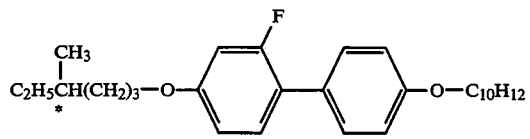

Using (s)-3-fluoro-4-bromo-(4′-methylhexyl)oxybenzene obtained in the above (b) in place of (s)-2-fluoro-4-bromo-(4′-methylhexyl)oxybenzene in Example 1-(d), an operation was carried out similarly whereby 1.2 g of (s)-4-decyloxy-2′-fluoro-4′-(4″-methylhexyl)oxybiphenyl was obtained.

The purity of this compound was at least 99% by liquid chromatography. This compound was confirmed to be the end product in view of its measurement by infra-red rays absorption spectrometry and its molecular ion peak found at 442 by mass spectrometry and in view of the relation to the starting materials used.

This compound was inserted into a Mettler hot stage FP-82 and its phase transition was observed under a polarization microscope. A result of the observation is shown in Table 1.

EXAMPLE 17

(a) Synthesis of

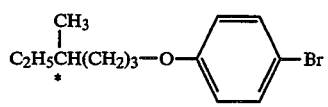

A reaction vessel was charged with 48.4 g of 4-bromophenol, 50 g of (s)-4-methylhexyl bromide, 65 g of K₂CO₃ and 700 ml of cyclohexanone, and the mixture was reacted together at 120°–130° C. until the starting materials disappeared (confirmed by gas chromatography). For this, 6 hours were required.

The reaction liquid was poured into water and extracted with ether. After that, the extract was washed with a diluted aqueous solution of NaOH and then with water to make the extract neutral. After drying the extract over Glauber's salt, the ether was removed by distillation and the residue was distilled under reduced pressure whereupon 66 g of (s)-4-bromo-(4'-methylhexyl)-oxybenzene was obtained.

b.p. 120°–123° C./0.5 mmHg
GLC at least 93%

(b) Synthesis of

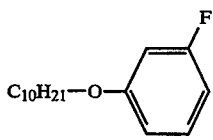

Using 3-fluorophenol in place of 4-bromophenol in Example 1-(a), an operation was carried out similarly whereby 19.5 g of 3-fluoro-decyloxybenzene was obtained.

b.p. 105°–108° C./0.3 mmHg
GLC at least 99%

(c) Synthesis of

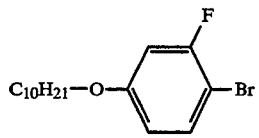

Using 3-fluoro-decyloxybenzene obtained in (b) in place of (s)-2-fluoro-(4'-methylhexyl)oxybenzene in Example 1-(c), an operation was carried out similarly whereby 18 g of 3-fluoro-4-bromo-decyloxybenzene was obtained.

b.p. 103°–110° C./0.5 mmHg
GLC 84% (others were structurally isomeric bromine compounds)

(d) Synthesis of

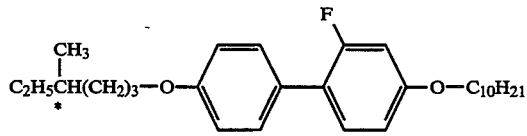

In Example 1-(d), the operation was carried out similarly except that (s)-4-bromo-(4'-methylhexyl)oxybenzene obtained in the above (a) was used in place of 4-bromo-decyloxybenzene while 3-fluoro-4-bromo-decyloxybenzene obtained in the above (c) was used in place of (s)-3-fluoro-4-bromo(4'-methylhexyl)oxybenzene, whereby 0.33 g of (s)-4-(4''-methylhexyl)oxy-2'-fluoro-4'-decyloxybiphenyl was obtained.

The purity of this compound was at least 99% by liquid chromatography. This compound was confirmed to be the end product in view of its measurement by infra-red rays absorption spectrometry and its molecular ion peak found at 442 by mass spectrometry and in view of the relation to the starting materials used.

This compound was inserted into a Mettler hot stage FP-82 and its phase transition was observed under a polarization microscope. A result of the observation is shown in Table 1.

EXAMPLE 18

(a) Synthesis of

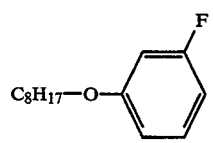

Except that in Example 1-(b) octyl bromide was used in place of (s)-methylhexyl bromide while 3-fluorophenol was used in place of 2-fluorophenol, the operation was carried out similarly whereby 18 g of 3-fluoro-octyloxybenzene was obtained.

(b) Synthesis of

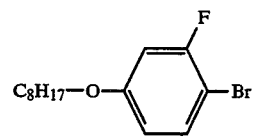

In Example 1-(c), the operation was carried out similarly except that 3-fluoro-octyloxybenzene obtained in (a) was used in place of 2-fluoro-(4'-methylhexyl)oxybenzene, whereby 18 g of 3-fluoro-4-bromo-octyloxybenzene was obtained.

b.p. 139°–142° C./0.9 mmHg (c) Synthesis of

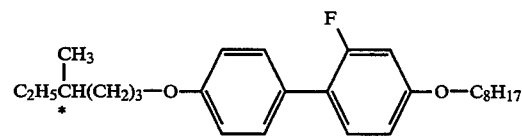

In Example 1-(d), the operation was carried out similarly except that (s)-4-bromo-(4'-methylhexyl)oxybenzene obtained in Example 17-(a) was used in place of 4-bromo-decyloxybenzene while 3-fluoro-4-bromo-octyloxybenzene obtained in (b) was used in place of (s)-2-fluoro-4-bromo-(4'-methylhexyl)oxybenzene, whereby (s)-4-(4''-methylhexyl)oxy-2'-fluoro-4'-octyloxybenzene was obtained.

Yield 0.5 g (3.7%)

The purity of this compound was at least 99% by liquid chromatography. This compound was confirmed to be the end product in view of its measurement by infra-red rays absorption spectrometry and its molecular ion peak found at 414 by mass spectrometry and in view of the relation to the starting materials used.

This compound was inserted into a Mettler hot stage FP-82 and its phase transition was observed under a polarization microscope. A result of the observation is shown in Table 1.

EXAMPLE 19

(a) Synthesis of

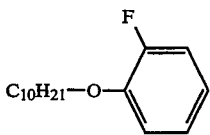

In Example 1-(b), the operation was carried out similarly except that decyl bromide was used in place of (s)-4-methylhexyl bromide, whereby 20 g of 2-fluoro-decyloxybenzene was obtained.

(b) Synthesis of

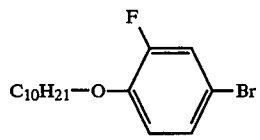

In Example 1-(c), the operation was carried out similarly except that 2-fluoro-decyloxybenzene obtained in (a) was used in place of (s)-2-fluoro-(4'-methylhexyl)oxybenzene, whereby 17.2 g of 2-fluoro-4-bromo-decyloxybenzene was obtained.
b.p. 147° C./0.7 mmHg
GLC at least 98%

(c) Synthesis of

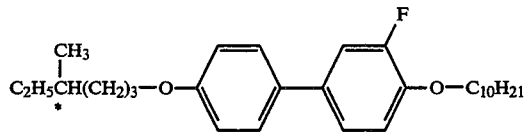

In Example 1-(d), the operation was carried out similarly except that (s)-4-bromo-(4'-methylhexyl)oxybenzene obtained in Example 17-(a) was used in place of 4-bromo-decyloxybenzene while 2-fluoro-4-bromo-decyloxybenzene obtained in (b) was used in place of (s)-2-fluoro-4-bromo-(4'-methylhexyl)oxybenzene, whereby 1.2 g of (s)-4-(4''-methylhexyl)oxy-3'-fluoro-4'-decyloxybiphenyl was obtained.

The purity of this compound was at least 99% by liquid chromatography. This compound was confirmed to be the end product in view of its measurement by infra-red rays absorption spectrometry and its molecular ion peak found at 442 by mass spectrometry and in view of the relation to the starting materials used.

This compound was inserted into a Mettler hot stage FP-82 and its phase transition was observed under a polarization microscope. A result of the observation is shown in Table 1.

EXAMPLE 20

(a) Synthesis of

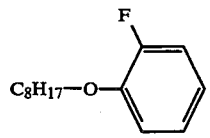

In Example 1-(b), the operation was carried out similarly except that octyl bromide was used in place of (s)-4-methylhexyl bromide, whereby 22 g of 2-fluoro-octyloxybenzene was obtained.

(b) Synthesis of

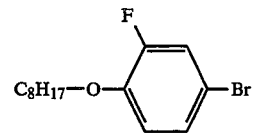

In Example 1-(c), the operation was carried out similarly except that 2-fluoro-octyloxybenzene obtained in (a) was used in place of (s)-2-fluoro-(4'-methylhexyl)oxybenzene, whereby 19.3 g of 2-fluoro-4-bromo-decyloxybenzene was obtained.
b.p. 122°-130° C./0.3-1.0 mmHg (c) Synthesis of

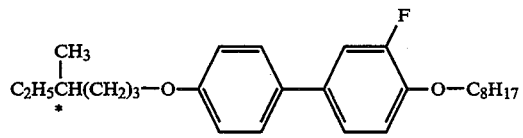

In Example 1-(d), the operation was carried out similarly except that (s)-4-bromo-(4'-methylhexyl)oxybenzene obtained in Example 17-(a) was used in place of 4-bromo-decyloxybenzene while 2-fluoro-4-bromo-octyloxybenzene obtained in (b) was used in place of (s)-2-fluoro-4-bromo-(4'-methylhexyl)oxybenzene, whereby 4.4 g of (s)-4-(4''-methylhexyl)oxy-3'-fluoro-4'-octyloxybiphenyl was obtained.

The purity of this compound was at least 99% by liquid chromatography. This compound was confirmed to be the end product in view of its measurement by infra-red rays absorption spectrometry and its molecular ion peak found at 414 by mass spectrometry and in view of the relation to the starting materials used.

This compound was inserted into a Mettler hot stage FP-82 and its phase transition was observed under a polarization microscope. A result of the observation is shown in Table 1.

EXAMPLE 21

Synthesis of

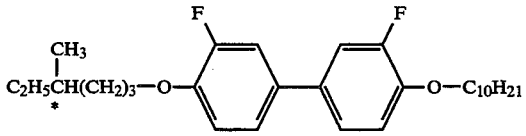

In Example 1-(d), the operation was carried out similarly except that (s)-2-fluoro-4-bromo-(4'-methylhexyl)oxybenzene obtained in Example 1-(c) was used in place of 4-bromo-decyloxybenzene while 2-fluoro-4-bromo-decyloxybenzene obtained in Example 19-(b) was used in place of (s)-2-fluoro-4-bromo-(4'-methylhexyl)oxybenzene, whereby 1.07 g of (s)-3,3'-difluoro-4-(4''-methylhexyl)oxy-4'-decyloxybiphenyl was obtained.

The purity of this compound was at least 99% by liquid chromatography. This compound was confirmed to be the end product in view of its measurement by infra-red rays absorption spectrometry and its molecular ion peak found at 460 by mass spectrometry and in view of the relation to the starting materials used.

This compound was inserted into a Mettler hot stage FP-82 and its phase transition was observed under a polarization microscope. A result of the observation is shown in Table 1.

EXAMPLE 22

Synthesis of

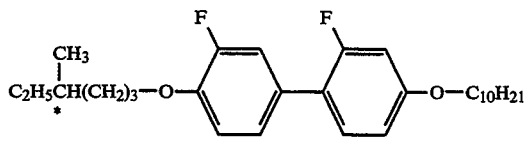

In Example 1-(d), the operation was carried out similarly except that (s)-2-fluoro-4-bromo-(4'-methylhexyl)oxybenzene obtained in Example 17-(a) was used in place of 4-bromo-decyloxybenzene while 3-fluoro-4-bromo-decyloxybenzene obtained in Example 17-(c) was used in place of (s)-2-fluoro-4-bromo-(4'-methylhexyl)oxybenzene, whereby 1.12 g of (s)-3,2'-difluoro-4-(4''-methylhexyl)oxy-4'-decyloxybiphenyl was obtained.

The purity of this compound was at least 99% by liquid chromatography. This compound was confirmed to be the end product in view of its measurement by infra-red rays absorption spectrometry and its molecular ion peak found at 460 by mass spectrometry and in view of the relation to the starting materials used.

This compound was inserted into a Mettler hot stage FP-82 and its phase transition was observed under a polarization microscope. A result of the observation is shown in Table 1.

EXAMPLE 23

(a) Synthesis of

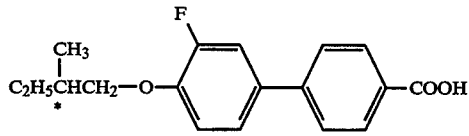

A reaction vessel was charged with 4.6 g of NaOH and 40 ml of water. To the mixture under agitation was added dropwise below 5° C. 6.5 g of bromine. After the addition, the mixture was stirred for 1.5 hours below 10° C. to prepare an aqueous solution of a hypobromite. A separate reaction vessel was charged with 1.95 g of (s)-3-fluoro-4-(2''-methylbutyl)oxy-4'-acetylbiphenyl obtained in Example 2-(e) and 25 ml of dioxane. To this mixture under agitation was added dropwise at room temperature, the previously prepared aqueous solution of the hypobromite. After the addition, the mixture was heated under heat for 3 hours at 50°–60° C. The reaction liquid was poured into an aqueous solution of sodium sulfite and the mixture was made acidic with hydrochloric acid. The precipitated crystals were collected by filtration, washed with water and dried whereupon (s)-3-fluoro-4-(2''-methylbutyl)oxy-4'-biphenylcarboxylic acid was obtained.

Yield 1.6 g (81.6%)

(b) Synthesis of

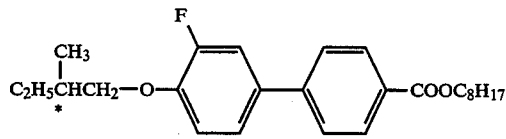

A reaction vessel was charged with 1.6 g of (s)-3-fluoro-4-(2''-methylbutyl)oxy-4'-biphenylcarboxylic acid obtained in (a) and 50 ml of benzene. To this mixture under agitation was added dropwise 2 g of thionyl chloride at room temperature, and the whole was refluxed for 6 hours. After completion of the reaction, excess thionyl chloride and benzene were distilled off, and 1.6 g of crude acid chloride was obtained by repeating addition of benzene to the residue and removal of the benzene by distillation.

A separate vessel was charged with 0.8 g of octyl alcohol, 20 ml of benzene and 1.0 g of pyridine. To the mixture under agitation at room temperature was added dropwise a solution of the previously prepared acid chloride in 20 ml of benzene, and the whole was refluxed for 7 hours. The reaction liquid was poured into water and extracted with benzene. The extract was washed with water and dried over Glauber's salt. The solvent was distilled off and the residue was purified by way of column chromatography on silica gel using hexane-benzene (4:1) as an eluent, and recrystallized from ethanol to obtain (s)-3-fluoro-4-(2''-methylbutyl)oxy-4'-biphenylcarboxylic acid octyl ester.

Yield 1.0 g (44.2%)

The purity of this compound was at least 99% by liquid chromatography. This compound was confirmed to be the end product in view of its measurement by infra-red rays absorption spectrometry and its molecular ion peak found at 414 by mass spectrometry and in view of the relation to the starting materials used.

This compound was inserted into a Mettler hot stage FP-82 and its phase transition was observed under a polarization microscope. A result of the observation is shown in Table 1.

EXAMPLE 24

(a) Synthesis of

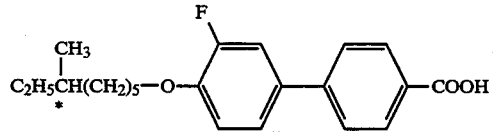

A reaction vessel was charged with 21.2 g of NaOH and 100 ml of water. To this mixture under agitation below 5° C. was added dropwise 29 g of bromine. After the addition, the mixture was stirred for 1.5 hours below 10° C. to prepare an aqueous solution of a hypobromite. In a separate vessel was charged with 11 g of (s)-3-fluoro-4-(6''-methyloctyl)oxy-4'-acetylbiphenyl obtained as an intermediate in Example 8-(a) and 100 ml of dioxane. To this mixture under agitation at room temperature was added dropwise the previously prepared aqueous hypobromite solution. After the addition, the mixture was heated for 3 hours at 50°–60° C. under agitation. The reaction liquid was poured into an aqueous solution of sodium sulfite and the mixture was made acidic with hydrochloric acid. The precipitated crystals were collected by filtration, washed with water and dried to obtain (s)-3-fluoro-4-(6" -methyloctyl)oxy-4'-biphenylcarboxylic acid.

Yield 9.85 g (88.7%)

(b) Synthesis of

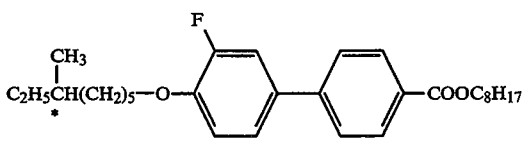

A reaction vessel was charged with 4.5 g of (s)-3-fluoro-4-(6"-methyloctyl)oxy-4'-biphenylcarboxylic acid obtained in (a) and 50 ml of benzene. To the mixture under agitation at room temperature was added dropwise 5 g of thionyl chloride, and the whole was refluxed for 11 hours. After completion of the reaction, excess thionyl chloride and benzene were distilled off, and 4.66 g of crude acid chloride was obtained by repeating addition of benzene to the residue and removal of the benzene by distillation.

A separate vessel was charged with 0.55 g of octyl alcohol, 20 ml of benzene and 0.43 g of pyridine. To the mixture under agitation at room temperature was added dropwise a solution of the previously prepared acid chloride in 20 ml of benzene, and the whole was refluxed for 13 hours. The reaction liquid was poured into water and extracted with benzene. The extract was washed with water and dried over Glauber's salt. The solvent was distilled off and the residue was purified by way of column chromatography on silica gel using hexane-benzene (4:1) as an eluent, and recrystallized from ethanol to obtain (s)-3-fluoro-4-(6"-methyloctyl)oxy-4'-biphenylcarboxylic acid octyl ester.

Yield 0.76 g (49%)

The purity of this compound was at least 98% by liquid chromatography. This compound was confirmed to be the end product in view of its measurement by infra-red rays absorption spectrometry and its molecular ion peak found at 470 by mass spectrometry and in view of the relation to the starting materials used.

This compound was inserted into a Mettler hot stage FP-82 and its phase transition was observed under a polarization microscope. A result of the observation is shown in Table 1.

EXAMPLES 25, 26 and 27

Synthesis of

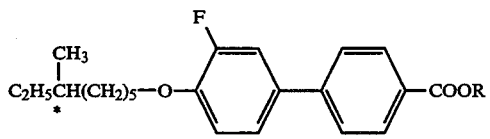

R = $C_4H_9$ (Example 25), $C_6H_{13}$ (Example 26), $C_{10}H_{21}$ (Example 27)

In Example 24-(b), the operation was carried out similarly except that 0.31 g of butanol, 0.43 g of hexanol or 0.66 g of decyl alcohol was used in place of 0.55 g of octanol, whereby 0.61 g (47.3%), 0.95 g (47.3%) or 1.04 g (57.9%) of the corresponding (s)-3-fluoro-4-(6"-methyloctyl)oxy-4"-biphenylcarboxylic acid butyl ester, (s)-3-fluoro-4-(6"-methyloctyl)oxy-4'-biphenylcarboxylic acid hexyl ester or (s)-3-fluoro-4-(6"-methyloctyl)oxy-4'-biphenylcarboxylic acid decyl ester, respectively, were obtained.

The purity of these compounds were at least 99% by liquid chromatography. These compounds were confirmed to be the end products in view of their measurement by infra-red rays absorption spectrometry and their molecular ion peaks found at 414, 442 and 498 by mass spectrometry and in view of the relation to the starting materials used.

These compounds were inserted into a Mettler hot stage FP-82 and their phase transition was observed under a polarization microscope. Results of the observation are shown in Table 1.

EXAMPLE 28

(a) Synthesis of

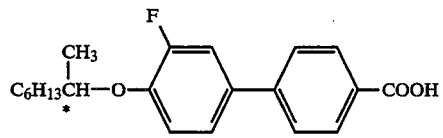

A reaction vessel was charged with 8.8 g of NaOH and 30 ml of water. To the mixture under agitation below 5° C. was added dropwise 14 g of bromine. After the addition, the mixture was stirred for 1.5 hours below 10° C. to prepare an aqueous solution of a hypobromite. A separate vessel was charged with 4.06 g (s)-3-fluoro-4-(1"-methylheptyl)oxy-4'-acetylbiphenyl obtained as an intermediate in Example 14-(a) and 75 ml of dioxane. To the mixture under agitation at room temperature was added dropwise a solution of the previously prepared aqueous solution of hypobromite, and the whole was heated for 5 hours at 50°-60° C. under agitation. The reaction liquid was poured into an aqueous solution of sodium sulfite and the mixture was made acidic with hydrochloric acid. The precipitated crystals were collected by filtration, washed with water and dried to obtain (s)-3-fluoro-4-(1"-methylheptyl)oxy-4'-biphenylcarboxylic acid was obtained.

Yield 4.07 g (99.8%)

(b) Synthesis of

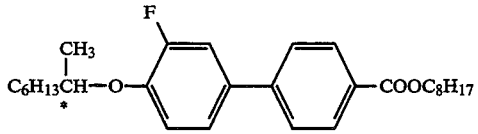

A reaction vessel was charged with 3.9 g of (s)-3-fluoro-4-(1"-methylheptyl)oxy-4'-biphenylcarboxylic acid obtained in (a) and 50 ml of benzene. To this mixture under agitation at room temperature was added dropwise 4 g of thionyl chloride, and the whole was refluxed for 12 hours. After completion of the reaction, excess thionyl chloride and benzene were distilled off, and 4.55 g of crude acid chloride was obtained by repeating addition of benzene to the residue and removal of the benzene by distillation.

A separate vessel was charged with 0.47 g of octyl alcohol, 20 ml of benzene and 0.52 g of pyridine. To the mixture under agitation at room temperature was added dropwise a solution of 1.2 g of the previously prepared acid chloride in 20 ml of benzene, and the whole was refluxed for 7 hours. The reaction liquid was poured into water and extracted with benzene. The extract was washed with water and dried over Glauber's salt. The solvent was distilled off and the residue was purified by way of column chromatography on silica gel using hexane-benzene (4:1) as an eluent, and recrystallized from ethanol to obtain (s)-3-fluoro-4-(1"-methylheptyl)oxy-4'-biphenylcarboxylic acid octyl ester.

Yield 1.16 g (yield rate: 77%)

The purity of this compound was at least 99% by liquid chromatography. This compound was confirmed to be the end product in view of its measurement by infra-red rays absorption spectrometry and its molecular ion peak found at 456 by mass spectrometry and in view of the relation to the starting materials used.

This compound was inserted into a Mettler hot stage FP-82 and its phase transition was observed under a polarization microscope. A result of the observation is shown in Table 1.

EXAMPLES 29 and 30

Synthesis of

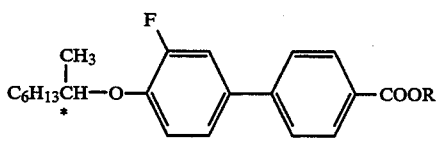

R = C$_6$H$_{13}$ (Example 29), C$_{10}$H$_{21}$ (Example 30)

In Example 28-(b), the operation was carried out similarly except that 0.37 g of hexanol or 0.58 g of decyl alcohol was used in place of 0.47 g of octanol, whereby 0.75 g (64.6%) or 1.28 g (78.0%) of the corresponding (s)-3-fluoro-4-(1"-methylheptyl)oxy-4'-(1"-methylheptyl)oxy-4'-biphenylcarboxylic acid hexyl ester and (s)-3-fluoro-4-(1"-methylheptyl)oxy-4'-biphenylcarboxylic acid decyl ester, respectively, were obtained.

The purity of these compounds were at least 99% by liquid chromatography. These compounds were confirmed to be the end products in view of their measurement by infra-red rays absorption spectrometry and their molecular ion peaks found at 428 and 484 by mass spectrometry and in view of the relation to the starting materials used.

These compounds were inserted into a Mettler hot stage FP-82 and their phase transition was observed under a polarization microscope. Results of the observation are shown in Table 1.

EXAMPLE 31

Synthesis of

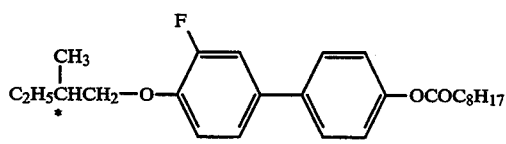

A reaction vessel was charged with 1.01 g of (s)-3-fluoro-4-(2"-methylbutyl)oxy-4'-hydroxybiphenyl obtained in Example 2-(f), 0.65 g of pyridine and 20 ml of benzene. To the mixture under agitation at room temperature was added dropwise a solution of 0.82 g of nonanoyl chloride in 5 ml of benzene, and the whole was refluxed for 4 hours under agitation. The reaction liquid was poured into water and extracted with benzene. The extract was washed with water, treated with ammonia water, washed with water and dried over Glauber's salt. The benzene was then distilled off and the residue was purified by way of column chromatography on silica gel using hexane-benzene (2:1) as an eluent whereby 0.66 g (43.1%) of (s)-3-fluoro-4-(2"-methylbutyl)oxy-4'-nonanoyloxybiphenyl was obtained.

The purity of this compound was at least 99% by liquid chromatography. This compound was confirmed to be the end product in view of its measurement by infra-red rays absorption spectrometry and its molecular ion peak found at 415 by mass spectrometry and in view of the relation to the starting materials used.

This compound was inserted into a Mettler hot stage FP-82 and its phase transition was observed under a polarization microscope. A result of the observation is shown in Table 1.

EXAMPLE 32

Synthesis of

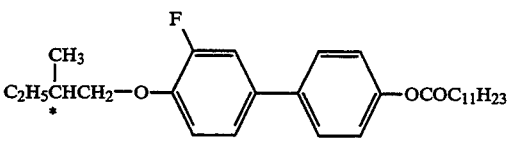

In Example 31, the operation was carried out similarly except that 1.01 g of dodecanoyl chloride was used in place of 0.82 g of nonanoyl chloride, whereby 1.23 g (55.8%) of (s)-3-fluoro-4-(2"-methylbutyl)oxy-4'-dodecanoyloxybiphenyl was obtained.

The purity of this compound was at least 99% by liquid chromatography. This compound was confirmed to be the end product in view of its measurement by infra-red rays absorption spectrometry and its molecular ion peak found at 457 by mass spectrometry and in view of the relation to the starting materials used.

This compound was inserted into a Mettler hot stage FP-82 and its phase transition was observed under a polarization microscope. A result of the observation is shown in Table 1.

EXAMPLE 33

Synthesis of

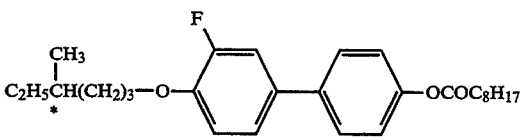

A reaction vessel was charged with 1.5 g of (s)-3-fluoro-4-(4"-methylhexyl)oxy-4'-hydroxybiphenyl obtained in Example 6-(a), 1.13 g of pyridine and 30 ml of benzene. To this mixture under agitation at room temperature was added dropwise a solution of 1.06 g of nonanoyl chloride in 10 ml of benzene, and the whole was refluxed for 14 hours. The reaction mixture was poured into water and extracted with benzene. The extract was washed with water treated with ammonia water, washed with water and dried over Glauber's salt. The benzene was distilled off and the residue was purified by way of column chromatography on silica gel using hexane-benzene (2:1) as an eluent, whereby 0.51 g (23.2%) of (s)-3-fluoro-4-(4"-methylhexyl)oxy-4'-nonanoyloxybiphenyl was obtained.

The purity of this compound was at least 98% by liquid chromatography. This compound was confirmed to be the end product in view of its measurement by infra-red rays absorption spectrometry and its molecular ion peak found at 442 by mass spectrometry and in view of the relation to the starting materials used.

This compound was inserted into a Mettler hot stage FP-82 and its phase transition was observed under a polarization microscope. A result of the observation is shown in Table 1.

EXAMPLES 34 and 35

Synthesis of

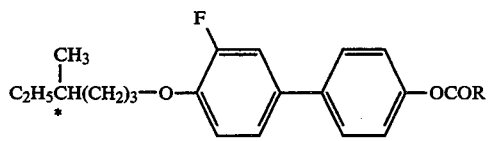

R=C$_6$H$_{13}$ (Example 34) C$_{11}$H$_{23}$ (Example 35)

In Example 33, the operation was carried out similarly except that 0.91 g of heptanoyl chloride or 1.30 g of dodecanoyl chloride was used in place of 1.06 g of nonanoyl chloride, whereby 1.16 g (56.3%) or 0.93 g (38.8%) of the corresponding (s)-3-fluoro-4-(4''-methylhexyl)oxy-4'-heptanoyloxybiphenyl or (s)-3-fluoro-4-(4''-methylhexyl)oxy-4'-dodecanoyloxybiphenyl, respectively, were obtained.

The purity of these compounds were at least 99% by HPLC. These compounds were confirmed to be the end products in view of their measurement by infra-red rays absorption spectrometry and their molecular ion peaks found at 414 and 484 by mass spectrometry and in view of the relation to the starting materials used.

These compounds were inserted into a Mettler hot stage FP-62 and their phase transition was observed under a polarization microscope. Results of the observation are shown in Table 1.

EXAMPLE 36

Synthesis of

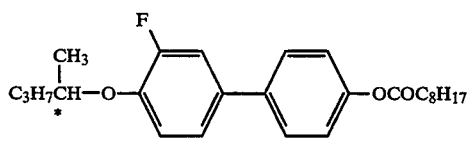

A reaction vessel was charged with 1.01 g (s)-3-fluoro- 4-(1''-methylbutyl)oxy-4'-hydroxybiphenyl obtained in Example 11-(a), 0.65 g of pyridine and 20 ml of benzene. To the mixture under agitation at room temperature was added dropwise a solution of 0.82 g of nonanoyl chloride in 5 ml of benzene, and the whole was refluxed for 4 hours under agitation. The reaction liquid was poured into water and extracted with benzene. The extract was washed with water, treated with ammonia water, washed with water and dried over Glauber's salt. The benzene was distilled off and the residue was purified by way of column chromatography on silica gel using hexanebenzene (2:1) as an eluent, whereby 0.57 g (37%) of (s)-3-fluoro-4-(1''-methylbutyl)oxy-4'-nonanoyloxybiphenyl was obtained.

The purity of this compound was at least 99% by liquid chromatography. This compound was confirmed to be the end product in view of its measurement by infra-red rays absorption spectrometry and its molecular ion peak found at 414 by mass spectrometry and in view of the relation to the starting materials used.

This compound was inserted into a Mettler hot stage FP-82 and its phase transition was observed under a polarization microscope. A result of the observation is shown in Table 1.

EXAMPLES 37 and 38

Synthesis of

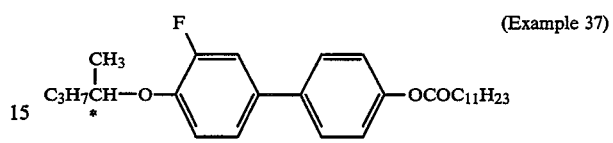
(Example 37)

Synthesis of

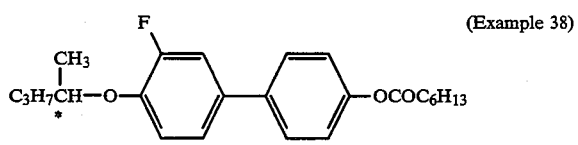
(Example 38)

In Example 36, the operation was carried out similarly except that 1.0 g of dodecanoyl chloride or 0.62 g of heptanoyl chloride was used in place of 0.82 g of nonanoyl chloride, whereby 0.49 g (29%) or 0.39 g (28%) of the corresponding (s)-3-fluoro-4-(1'''-methylbutyl)oxy-4'-dodecanoyloxybiphenyl or (s)-3-fluoro-4-(1'''-methylbutyl)oxy-4'-heptanoylchloride, respectively, were obtained.

The purity of these compounds were at least 99% by HPLC. These compounds were confirmed to be the end products in view of their measurement by infra-red rays absorption spectrometry and their molecular ion peaks found at 456 and 386 by mass spectrometry and in view of the relation to the starting materials used.

These compounds were inserted into a Mettler hot stage FP-82 and their phase transition was observed under a polarization microscope. Results of the observation are shown in Table 1.

EXAMPLE 39

(a) Synthesis of

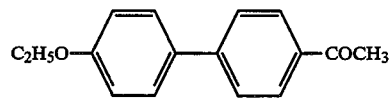

A reaction vessel was charged with 230 g of 4-hydroxy-4'-acetylbiphenyl, 164 g of ethyl bromide, 276 g of potassium carbonate and 1.7 l of cyclohexanone. The mixture was reacted together under agitation for 3 hours at 65°–70° C. and then for 6 hours at 95°–100° C. The reaction liquid was filtered and the resultant solid matter was washed with benzene. The filtrate and the washing liquid were combined, washed with water and dried over Glauber's salt, The solvents were distilled off and the residue was recrystallized from a mixed solvent of acetone-methanol to obtain 4-ethoxy-4'-acetylbiphenyl.

Yield 240 g (93%)

GLC 90.1%

(b) Synthesis of

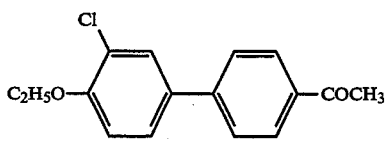

A reaction vessel was charged with 240 g of 4-ethoxy-4'-acetylbiphenyl obtained in (a), 1.8 l of acetic acid, 25 ml of concentrated hydrochloric acid and 125 g of dichloramine-T. The mixture was reacted together at 100° C. under agitation while occasionally adding dichloramine-T and concentrated hydrochloric acid, until the starting materials disappeared (confirmed by GLC). For this, 56 hours were required.

The reaction liquid was poured into water and washed with water by decantation until the washed liquid became neutral. The reaction product was extracted with methylene chloride and the extract was dried over Glauber's salt. The solvents were distilled off and the residue was recrystallized from a mixed solvent of ethanolmethyl ethyl ketone and then from hexane to obtain 3-chloro-4-ethoxy-40'-acetylbiphenyl.

Yield 78 g (28%)
GLC 80%

(c) Synthesis of

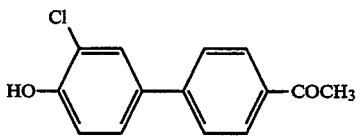

A reaction vessel was charged with 78 g of 3-chloro-4-ethoxy-4'-acetylbiphenyl obtained in (b), 780 ml of 48% hydrobromic acid and 1.2 l of acetic acid, and the mixture was heated under agitation for 23 hours at 100°-110° C. The reaction liquid was poured into water and the precipitated crystals were collected by filtration, washed with water and purified by way of column chromatography on silica gel using methylene chloride as an eluent, whereby 3-chloro-4-hydroxy-4'-acetylbiphenyl was obtained.

Yield 27.9 g (40%)
GLC 98%

(d) Synthesis of

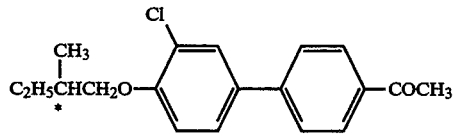

A reaction vessel was charged with 7.5 g of 3-chloro-4-hydroxy-4'-acetylbiphenyl obtained in (c), 6.8 g of (s)-2-methylbutyl bromide, 6.2 g of potassium carbonate and 150 ml of cyclohexanone, and the mixture was heated under agitation for 23 hours at 90°-100° C. The reaction liquid was filtered and the resultant solid matter was washed with benzene. The filtrate was combined with the washed liquid, washed with water and dried over Glauber's salt. The solvents were distilled off and the residue was recrystallized from acetone-methanol to obtain (s)-3-chloro-4-(2''-methylbutyl)oxy-4'-acetylbiphenyl.

Yield 6.9 g (73%)
GLC 98.5%

(e) Synthesis of

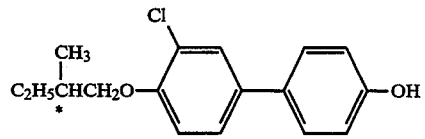

A reaction vessel was charged with 6.9 g of (s)-3-chloro-4-(2''-methylbutyl)oxy-4'-acetylbiphenyl obtained in (d), 40 g of 68% formic acid and 60 ml of methylene chloride. To this mixture under agitation at room temperature were successively added dropwise 15 g of acetic anhydride, 1 ml of concentrated sulfuric acid and 15 g of 35% hydrogen peroxide. After the addition, the mixture was refluxed under agitation while occasionally adding 35% hydrogen peroxide thereto until the starting materials disappeared by TLC (Kieselgel 60 F 254, developing liquid: benzene). The reaction liquid was poured into water and the mixture was stirred for 1 hour. The organic layer was washed with water until the washing liquid became neutral, and then dried over Glauber's salt. The solvents were distilled off, and 80 ml of ethanol and 15 ml of an aqueous 35% caustic potash solution to the resultant residue. The mixture was refluxed under agitation for 5 hours. The reaction liquid was poured into water and the mixture was made acidic with hydrochloric acid and then extracted with ether. The extract was washed with water and dried over Glauber's salt. The solvents were distilled off and the residue was purified by way of column chromatography on silica gel whereby (s)-3-chloro-4-(2''-methylbutyl)oxy-4'-hydroxybiphenyl was obtained.

Yield 4.5 g (68.4%)

(f) Synthesis of

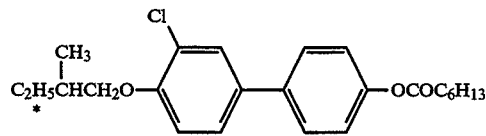

A reaction vessel was charged with 0.8 g of (s)-3-chloro-4-(2''-methylbutyl)oxy-4'-hydroxybiphenyl obtained in (e), 1 ml of pyridine and 25 ml of benzene. To the mixture under agitation at room temperature was added dropwise a solution of 0.6 g of heptanoyl chloride in 5 ml of benzene, and the whole was refluxed for 4 hours under agitation. The reaction liquid was poured into water and extracted with benzene. The extract was washed with water, treated with ammonia water, washed with water and then dried over Glauber's salt. The benzene was distilled off and the residue was purified by way of column chromatography on silica gel using hexane-benzene (2:1) as an eluent, whereby (s)-3-chloro-4-(2''-methylbutyl)oxy-4'-heptanoyloxybiphenyl was obtained.

Yield 0.58 g (50%)

The purity of this compound was at least 99% by HPLC. This compound was confirmed to be the end product in view of its measurement by IR absorption spectrometry and its molecular ion peak found at 402 by mass spectrometry and in view of the relation to the starting materials used.

This compound was inserted into a Mettler hot stage EP-82 and its phase transition was observed under a polarization microscope. A result of the observation is shown in Table 1.

EXAMPLE 40

Synthesis of

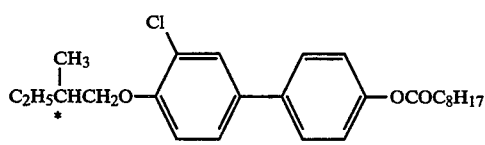

In Example 39-(f), the operation was carried out similarly except that 0.7 g of nonanoyl chloride was used in place of 0.6 g of heptanoyl chloride, whereby (s)-3-chloro-4-(2''-methylbutyl)oxy-4'-nonanoyloxybiphenyl was obtained.

Yield 0.75 g (65%)

The purity of this compound was at least 98% by HPLC. This compound was confirmed to be the end product in view of its measurement by IR absorption spectrometry and its molecular ion peak found at 430 by mass spectrometry and in view of the relation to the starting materials used.

This compound was inserted into a Mettler hot stage FP-82 and its phase transition was observed under a polarization microscope. A result of the observation is shown in Table 1.

EXAMPLE 41

Synthesis of

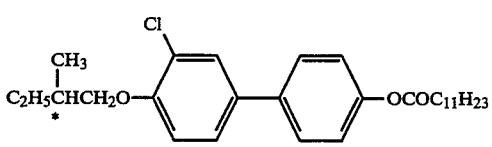

In Example 39-(f), the operation was carried out similarly except that 0.88 g of dodecanoyl chloride was used in place of 0.6 g of heptanoyl chloride, whereby (s)-3-chloro-4-(2''-methylbutyl)oxy-4'-dodecanoyloxybiphenyl was obtained.

Yield 0.73 g (56%)

The purity of this compound was at least 99% by HPLC. This compound was confirmed to be the end product in view of its measurement by IR absorption spectrometry and its molecular ion peak found at 472 by mass spectrometry and in view of the relation to the starting materials used.

This compound was inserted into a Mettler hot stage FP-82 and its phase transition was observed under a polarization microscope. A result of the observation is shown in Table 1.

EXAMPLE 42

(a) Synthesis of

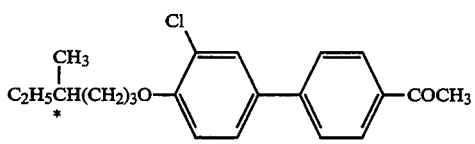

In Example 39-(d), the operation was carried out similarly except that 8.1 g of (s)-4-methylhexyl bromide was used in place of 6.8 g of (s)-2-methylbutyl bromide, whereby (s)-3-chloro-4-(4''-methylhexyl)oxy-4'-acetylbiphenyl was obtained.

Yield 9.2 g (89%)
GLC 99.2%

(b) Synthesis of

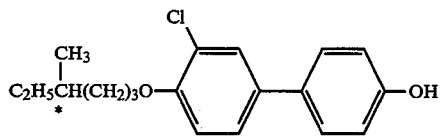

In Example 39-(e), the operation was carried out similarly except that 7.6 g of (s)-3-chloro-4-(4''-methylhexyl)oxy-4'-acetylbiphenyl obtained in (a) was used in place of 6.9 g of (s)-3-chloro-4-(2''-methylbutyl)oxy-4-acetylbiphenyl, whereby (s)-3-chloro-4-(4''-methylhexyl)oxy-4'-hydroxybiphenyl was obtained.

Yield 3.7 g (53.4%)
GLC 96% c) Synthesis of

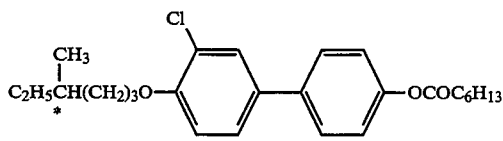

In Example 39-(f), the operation was carried out similarly except that 0.9 g of (s)-3-chloro-4-(4''-methylhexyl)oxy-4'-hydroxybiphenyl obtained in (b) was used in place of 0.8 g of (s)-3-chloro-4-(2''-methylbutyl)oxy-4'-hydroxybiphenyl, whereby (s)-3-chloro-4-(4''-methylhexyl)oxy-4'-heptanoyloxybiphenyl was obtained.

Yield 0.78 g (64%)

The purity of this compound was at least 99% by HPLC. This compound was confirmed to be the end product in view of its measurement by IR absorption spectrometry and its molecular ion peak found at 430 by mass spectrometry and in view of the relation to the starting materials used.

This compound was inserted into a Mettler hot stage FP-82 and its phase transition was observed under a polarization microscope. A result of the observation is shown in Table 1.

EXAMPLE 43

Synthesis of

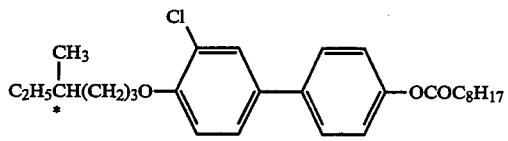

In Example 39-(f), the operation was carried out similarly except that 0.9 of (s)-3-chloro-4-(4″-methylhexyl)oxy-4′-hydroxybiphenyl obtained in (b) was used in place of 0.8 g of (s)-3-chloro-4-(2″-methylbutyl)oxy-4′-hydroxybiphenyl while 0.7 g of nonanoyl chloride was used in place of 0.6 g of heptanoyl chloride, whereby (s)-3-chloro-4-(4″-methylhexyl)oxy-4′-nonanoyloxybiphenyl was obtained.

Yield 0.91 g (71%)

The purity of this compound was at least 98% by HPLC. This compound was confirmed to be the end product in view of its measurement by IR absorption spectrometry and its molecular ion peak found at 456 by mass spectrometry and in view of the relation to the starting materials used.

This compound was inserted into a Mettler hot stage FP-82 and its phase transition was observed under a polarization microscope. A result of the observation is shown in Table 1.

EXAMPLE 44

Synthesis of

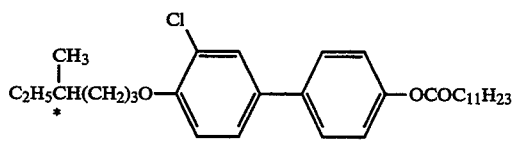

In Example 39-(f), the operation was carried out similarly except that 0.9 g of (s)-3-chloro-4-(4″-methylhexyl)oxy-4′-hydroxybiphenyl obtained in (b) was used in place of 0.8 g of (s)-3-chloro-4-(2″-methylbutyl)oxy-4′-hydroxybiphenyl while 0.9 g of dodecanoyl chloride was used in place of 0.6 g of heptanoyl chloride, whereby (s)-3-chloro-4-(4″-methylhexyl)oxy-4′-dodecanoyloxybiphenyl was obtained.

Yield 0.96 g (68.5%)

The purity of this compound was at least 98% by HPLC. This compound was confirmed to be the end product in view of its measurement by IR absorption spectrometry and its molecular ion peak found at 500 by mass spectrometry and in view of the relation to the starting materials used.

This compound was inserted into a Mettler hot stage FP-82 and its phase transition was observed under a polarization microscope. A result of the observation is shown in Table 1.

EXAMPLE 45

Synthesis of

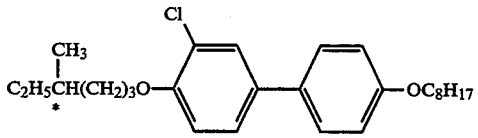

A reaction vessel was charged with 1.0 g of (s)-3-chloro-4-(4″-methylhexyl)oxy-4′-hydroxybiphenyl obtained in Example 42-(b), 1.4 g of octyl bromide, 1.0 g of potassium carbonate and 25 ml of cyclohexanone, and the mixture was reacted together under agitation for 13 hours at 70°-80° C. The reaction liquid was filtered and the resultant solid matter was washed with benzene. The filtrate was combined with the washing liquid, washed with water and dried over Glauber's salt. The solvents were removed and the residue was recrystallized from a mixed solvent of acetone-methanol-benzene to obtain (s)-3-chloro-4-(4″-methylhexyl)oxy-4′-octyloxybiphenyl.

Yield 1.1 g (81.5%)

The purity of this compound was at least 99% by HPLC. This compound was confirmed to be the end product in view of its measurement by IR absorption spectrometry and its molecular ion peak found at 430 by mass spectrometry and in view of the relation to the starting materials used.

This compound was inserted into a Mettler hot stage FP-82 and its phase transition was observed under a polarization microscope. A result of the observation is shown in Table 1.

EXAMPLE 46

Synthesis of

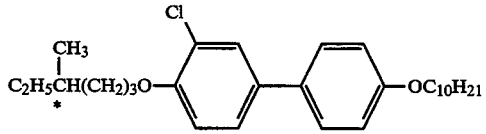

In Example 45, the operation was carried out similarly except that 1.6 g of decyl bromide was used in place of 1.4 g of octyl bromide, whereby (s)-3-chloro-4-(4″-methylhexyl)oxy-4′-decyloxybiphenyl was obtained.

Yield 1.12 g (78.6%)

The purity of this compound was at least 99% by HPLC. This compound was confirmed to be the end product in view of its measurement by IR absorption spectrometry and its molecular ion peak found at 458 by mass spectrometry and in view of the relation to the starting materials used.

This compound was inserted into a Mettler hot stage FP-82 and its phase transition was observed under a polarization microscope. A result of the observation is shown in Table 1.

EXAMPLE 47

(a) Synthesis of

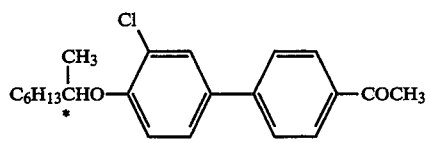

A reaction vessel was charged with 9.4 g of 3-chloro-4-hydroxy-4'-acetylbiphenyl obtained in Example 39-(c), 15.0 g of (s)-1-methylheptyl bromide, 10 g of potassium carbonate and 150 ml of cyclohexanone, and the mixture was heated under agitation for 13 hours at 80°–90° C. The reaction liquid was filtered and the resultant solid matter was washed with benzene. The filtrate was combined with the washing liquid, washed with water and dried over Glauber's salt. The solvents were distilled off to obtain a residue [crude (s)-3-chloro-4-(1''-methylheptyl)oxy-4'-acetylbiphenyl, GLC 93%], which was used as such for the next step.

(b) Synthesis of

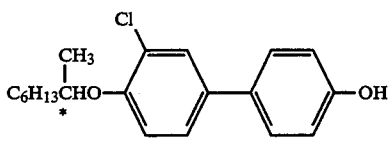

A reaction vessel was charged with the residue obtained in (a) [crude (s)-3-chloro-4-(1''-methylheptyl)oxy-4'-acetylbiphenyl], 50 g of 88% formic acid and 120 ml of methylene chloride. To the mixture under agitation at room temperature were successively added dropwise 21 g of acetic anhydride, 1 ml of concentrated sulfuric acid and 21 g of 35% hydrogen peroxide. After the addition, the mixture was refluxed under agitation while occasionally adding 35% hydrogen peroxide until the starting materials disappeared by TLC (Kieselgel 60F 254, developing liquid:benzene). The reaction liquid was poured into water and stirred for 1 hour. The organic layer was washed with water until the washing liquid became neutral, and then dried over Glauber's salt. The solvents were distilled off, and 100 ml of ethanol and 20 ml of an aqueous 35% caustic potash solution were added to the resultant residue. The mixture was refluxed under agitation for 5 hours and the reaction liquid was poured into water. The mixture was made acidic with hydrochloric acid and extracted with ether. The extract was washed with water and dried over Glauber's salt. The solvent was distilled off and the residue was purified by column chromatography on silica gel whereby (s)-3-chloro-4-(1''-methylheptyl)oxy-4'-hydroxybiphenyl was obtained.

Yield 5.4 g [46.7%, a total yield from (a)]
GLC 99.8%

(c) Synthesis of

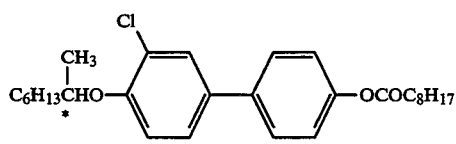

In Example 39-(f), the operation was carried out similarly except that 0.93 g of (s)-3-chloro-4-(1'''-methylheptyl)oxy-4'-hydroxybiphenyl obtained in (b) was used in place of 0.8 g of (s)-3-chloro-4-(2''-methylbutyl)oxy-4'-hydroxybiphenyl while 0.7 g of nonanoyl chloride was used in place of 0.6 g of heptanoyl chloride, whereby (s)-3-chloro-4-(1''-methylheptyl)oxy-4'-nonanoyloxybiphenyl was obtained.

Yield 0.41 g (30.8%)

The purity of this compound was at least 98% by HPLC. This compound was confirmed to be the end product in view of its measurement by IR absorption spectrometry and its molecular ion peak found at 472 by mass spectrometry and in view of the relation to the starting materials used.

This compound was inserted into a Mettler hot stage FP-82 and its phase transition was observed under a polarization microscope. A result of the observation is shown in Table 1.

EXAMPLE 48

(a) Synthesis of

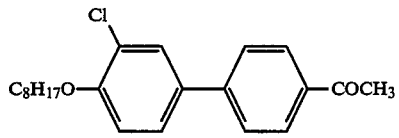

In Example 39-(d), the operation was carried out similarly except that 8.7 g of octyl bromide was used in place of 6.8 g of (s)-2-methylbutyl bromide, whereby 3-chloro-4-octyloxy-4'-acetylbiphenyl was obtained.

Yield 8.5 g (79%)
GLC 93.5%

(b) Synthesis of

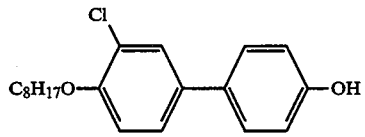

In Example 39-(e), the operation was carried out similarly except that 7.9 g of 3-chloro-4-octyloxy-4'-acetylbiphenyl obtained in (a) was used in place of 6.9 g of (s)-3-chloro-4-(2''-methylbutyl)oxy-4'-acetylbiphenyl, whereby 3-chloro-4-octyloxy-4'-hydroxybiphenyl was obtained.

Yield 5.3 g (72.7%)

(c) Synthesis of

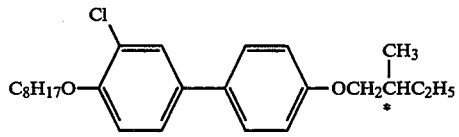

A reaction vessel was charged with 1.0 g of 3-chloro-4-octyloxy-4'-hydroxybiphenyl obtained in this Example (b), 0.8 g of (s)-2-methylbutyl bromide, 1.0 g of potassium carbonate and 25 ml of cyclohexanone, and the mixture was reacted together under agitation for 13 hours at 80°–90° C. The reaction liquid was filtered and the resultant solid matter was washed with benzene.

The filtrate was combined with the washing solution, washed with water and dried over Glauber's salt. The solvents were distilled off and the residue was recrystallized from a mixed solvent of acetone-methanol-benzene to obtain (s)-3-chloro-4-octyloxy-4'-(2'''-methylbutyl)oxybiphenyl.

Yield 0.6 g (50%)

The purity of this compound was at least 99% by HPLC. This compound was confirmed to be the end product in view of its measurement by IR absorption spectrometry and its molecular ion peak found at 402 by mass spectrometry and in view of the relation to the starting materials used.

This compound was inserted into a Mettler hot stage FP-82 and its phase transition was observed under a polarization microscope. A result of the observation is shown in Table 1.

EXAMPLE 49

Synthesis of

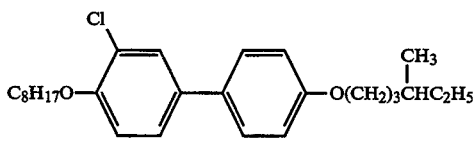

In Example 48-(c), the operation was carried out similarly except that 0.95 g of (s)-4-methylhexyl bromide was used in place of 0.8 g of (s)-2-methylbutyl bromide, whereby (s)-3-chloro-4-octyloxy-4'-(4''-methylhexyl)oxybiphenyl was obtained.

Yield 1.1 g (85%)

The purity of this compound was at least 99% by HPLC. This compound was confirmed to be the end product in view of its measurement by IR absorption spectrometry and its molecular ion peak found at 430 by mass spectrometry and in view of the relation to the starting materials used.

This compound was inserted into a Mettler hot stage FP-82 and its phase transition was observed under a polarization microscope. A result of the observation is shown in Table 1.

EXAMPLE 50

Synthesis of

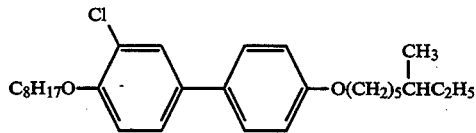

In Example 48-(c), the operation was carried out similarly except that 1.1 g of (s)-6-methyloctyl bromide was used in place of 0.8 g of (s)-2-methylbutyl bromide, whereby (s)-3-chloro-4-oxtyloxy-4'-(6''-methyloctyl)oxybiphenyl was obtained.

Yield 0.78 g (57%)

The purity of this compound was at least 99% by HPLC. This compound was confirmed to be the end product in view of its measurement by IR absorption spectrometry and its molecular ion peak found at 458 by mass spectrometry and in view of the relation to the starting materials used.

This compound was inserted into a Mettler hot stage FP-82 and its phase transition was observed under a polarization microscope. A result of the observation is shown in Table 1.

EXAMPLE 51

Using the compounds obtained in Examples 6 and 38 of the present invention, their response speed was measured according to the following method: A thin film of polyvinyl alcohol was coated on two panels of a glass basal plate with a transparent electrodes of indium oxide, and a rubbing treatment was made in a definite direction. On one panel of the basal plate was formed a spacer of $3\mu$ in thickness using a photoresist of negative type. This basal plate was combined with the other basal plate so as to make their direction of rubbing parallel to compose an element for evaluation. In this manner, two sets of the element were prepared. The elements were enclosed under reduced pressure with the compounds obtained in Examples 6 and 38 in the state of isotropic liquid to prepare liquid crystalline elements.

This liquid crystalline element was set in a polarization microscope provided with a hot stage, and the temperature of the element was lowered by 0.1 degree per minute from the state of isotropic liquid. After obtaining a monodomain in a visual field of the microscope, change in intensity of transmission light in case of applying a square wave of 200 Hz to the element was measured by using photodiodes, a photosenser amplifier and a digital storage scope. A result of the measurement is shown below.

| Compound | Response time | Voltage applied | Measurement temperature |
| --- | --- | --- | --- |
| Compound of Example 6 | 380 $\mu$sec | 10 V | 69° C. |
| Compound of Example 38 | 380 $\mu$sec | 50 V | 6.9° C. |

EXAMPLE 52

The compound obtained in Example 1 and the compound obtained in Example 34 were mixed in a ratio of 1:1 to prepare a liquid crystalline composition. On lowering the temperature, this composition changed from I to SmC* at 71° C. and from SmC* to C at 29.5° C. so that the range of temperature for the SmC* phase was 41.5 degrees. This liquid crystalline composition was enclosed in a liquid crystalline cell prepared by applying polyvinyl alcohol onto the surface of two glass basal plates provided with transparent electrodes, subjecting the plates to a rubbing treatment, and combining the plates so that their direction of rubbing might be parallel and the thickness of the cell might become 3 $\mu$m, and the composition was gradually cooled from the state of isotropic liquid to SmC*.

This liquid crystalline element was interposed between two polarization panels. When a 20 Hz triangle wave of 20 V was applied to the element, a distinct switching action was detected.

This liquid crystalline composition is a ferroelectric smectic liquid crystalline composition utilizable for electro-optical elements.

EXAMPLE 53

The compound obtained in Example 1 and the compound obtained in Example 44 were mixed in a ratio of 1:1 to prepare a liquid crystalline composition, which was then inserted into a Mettler hot stage FP-82 and observed under a polarization microscope to check the phase transition of the composition. It was found that the SmC* phase existed within the range of 38°-63° C. and that the range of temperature for the SmC* phase of this composition was broadened as compared with that of the individual compounds. This composition was enclosed in a liquid crystalline cell prepared by applying polyvinyl alcohol onto the surface of two glass basal plates provided with transparent electrodes, subjecting the plates to a rubbing treatment, and combining the plates so that their direction of rubbing might be parallel and the thickness of the cell might become 3 μm, and the composition was gradually cooled from the state of isotropic liquid to SmC*. This liquid crystalline element was interposed between two polarization panels. When a 20 Hz triangle wave of 20 V was applied to the element, a distinct switching action was detected. This liquid crystalline composition is a ferroelectric smectic liquid crystalline composition utilizable for electro-optical elements.

TABLE 1

| Example No. | Phase transition temperature (°C.) of the compounds obtained in Examples | | | | |
|---|---|---|---|---|---|
| | C | $S_X$ | $S_{C^*}$ | $S_A$ | Cho | I |
| 1 | .56 | | .69 | | | · |
| 2 | .52 | | (.51.5) | .61 | | · |
| 3 | .76.5 | | | | | · |
| 4 | .53 | | (.45) | .61 | | · |
| 5 | .63 | | | (.59) | | · |
| 6 | .66.5 | | .72 | | | · |
| 7 | .81 | | | | | · |
| 8 | .54 | .67.5 | .75 | | | · |
| 9 | .71 | | .72 | .74 | | · |
| 10 | .56 | | .73.5 | | | · |
| 11 | .36 | | (.21) | | | · |
| 12 | .38.5 | | (.25) | | | · |
| 13 | .50.8 | | | | | · |
| 14 | .46 | | | | | · |
| 15 | .36 | | | | | · |
| 16 | .25 | | (.24) | | .38 | · |
| 17 | .24 | | .28 | .36 | .40 | · |
| 18 | .6 | | .28 | .42 | | · |
| 19 | .60 | | (.59) | | | · |
| 20 | .65.8 | | | | | · |
| 21 | .56 | | | | | · |
| 22 | .5.5 | | (.4) | .36 | | · |
| 23 | .33 | | | | | · |
| 24 | .35.5 | | (.36) | .39 | | · |
| 25 | .47.5 | | | (.37) | | · |
| 26 | .32 | | (.32) | .38 | | · |
| 27 | .33 | | (.36) | .39 | | · |
| 28 | · | | On lowering temperature, non-crystal at −20° C. | | | · |
| 29 | · | | | | | · |
| 30 | · | | | | | · |
| 31 | .44 | | .56 | | | · |
| 32 | .56.5 | | .62 | | | · |
| 33 | .49 | | .76 | | | · |
| 34 | .63 | | .74 | | | · |
| 35 | .54 | | .78 | | | · |
| 36 | .28 | | (.17) | (.23) | | · |
| 37 | .34 | | (.30) | .34.5 | | · |
| 38 | .20.5 | | (.9.5) | | | · |
| 39 | .25 | | (.14.5) | (.16) | | · |
| 40 | .23 | | (.23.5) | .28 | | · |
| 41 | .39 | | (.31) | (.37.5) | | · |
| 42 | .34 | | .50 | | | · |
| 43 | .23.5 | | .56.5 | | | · |
| 44 | .48.5 | | .60.5 | | | · |
| 45 | .48 | | (.45) | .50 | | · |
| 46 | .47 | | | (.42.5) | | · |
| 47 | · | | On lowering temperature, non-crystal at −20° C. | (.−8) | | · |
| 48 | .28 | | | (.−0.6) | | · |
| 49 | .31 | | .33.5 | .34 | | · |
| 50 | .36 | | .45 | | | · |

We claim:

1. An optically active biphenyl compound for use in liquid crystal mixtures having a broad chiral smectic C phase at about room temperature and having the formula:

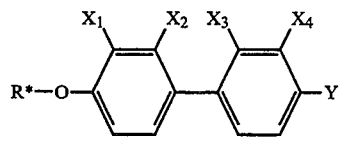

wherein R* is an alkyl group having an asymmetric carbon atom and 4-14 carbon atoms, any one or two of $X_1$, $X_2$, $X_3$ and $X_4$ is/are a fluorine or chlorine atom/atoms and the others are hydrogen atoms, and Y is OR or OCOR where R is an alkyl group with 3-14 carbon atoms.

2. The biphenyl compound according to claim 1, wherein any one or two of $X_1$, $X_2$, $X_3$ and $X_4$ in the above formula (I) is/are a fluorine atom/atoms and the others are hydrogen atoms.

3. The biphenyl compound according to claim 1, wherein any one or two of $X_1$, $X_2$, $X_3$ and $X_4$ in the above formula (I) is/are a chlorine atom/atoms and the others are hydrogen atoms.

4. A liquid crystalline composition containing at least one optically active biphenyl compound having a liquid crystalline phase and a broad chiral smectic C phase at about room temperature and having the formula:

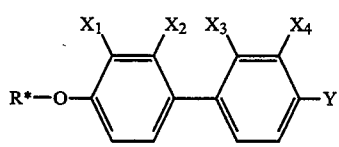

wherein R* is an alkyl group having an asymmetric carbon atom and 4-14 carbon atoms, any one or two of $X_1$, $X_2$, $X_3$ and $X_4$ is/are a fluorine or chlorine atom/atoms and the others are hydrogen atoms, and Y is OR or OCOR where R is an alkyl group with 3-14 carbon atoms.

5. The liquid crystalline composition according to claim 4, wherein any one or two of $X_1$, $X_2$, $X_3$ and $X_4$ in the above formula (I) is/are a fluorine atom/atoms and the others are hydrogen atoms.

6. The liquid crystalline composition according to claim 4, wherein any one or two of $X_1$, $X_2$, $X_3$ and $X_4$ in the above formula (I) is/are a chlorine atom/atoms and the others are hydrogen atoms.

7. A liquid crystal display element comprising a liquid crystalline composition containing a mixture of at least two optically active biphenyl compounds having a liquid crystalline phase and a broad chiral smectic C phase at about room temperature and having the formula

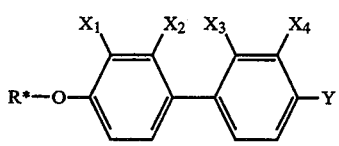

wherein R* is an alkyl group having an asymmetric carbon atom and 4-14 carbon atoms, any one or two of $X_1$, $X_2$, $X_3$, and $X_4$ is/are a fluorine or chlorine atom/atoms and the others are hydrogen atoms, and Y is OR or OCOR where R is an alkyl group with 3-14 carbon atoms.

8. The liquid crystal display element according to claim 7 comprising a liquid crystalline composition containing a mixture of (s)-4-decyloxy-3'-fluoro-4'-(4"-methylhexyl)oxybiphenyl and (s)-3-fluoro-4-(4" methylhexyl)oxy-4'-heptanoyloxybiphenyl or (s)-3-chloro-4-(4" methylhexyl)oxy-4'-dodecanoyloxy biphenyl.

* * * * *